(12) United States Patent
Farber et al.

(10) Patent No.: US 11,891,374 B2
(45) Date of Patent: Feb. 6, 2024

(54) DERIVATIZED BENZIMIDAZOLE COMPOUNDS, THEIR SALTS, THEIR COMPLEXES, THEIR PHARMACEUTICAL COMPOSITIONS AND METHODS FOR USING THEM FOR ANTIGERIATRIC ACTIONS

(71) Applicants: Boris Farber, Brooklyn, NY (US); Artur Viktorovich Martynov, Kharkov (UA); Serhii Ivanovych Merzlikin, Kharkov (UA)

(72) Inventors: Boris Farber, Brooklyn, NY (US); Artur Viktorovich Martynov, Kharkov (UA); Serhii Ivanovych Merzlikin, Kharkov (UA)

(*) Notice: Subject to any disclaimer, the term of this patent is extended or adjusted under 35 U.S.C. 154(b) by 0 days.

(21) Appl. No.: 17/256,848

(22) PCT Filed: Jan. 17, 2020

(86) PCT No.: PCT/RU2020/000019
§ 371 (c)(1),
(2) Date: Nov. 17, 2022

(87) PCT Pub. No.: WO2021/145785
PCT Pub. Date: Jul. 22, 2021

(65) Prior Publication Data
US 2023/0174505 A1    Jun. 8, 2023

(51) Int. Cl.
*C07D 401/06* (2006.01)
*A61P 43/00* (2006.01)

(52) U.S. Cl.
CPC ............ *C07D 401/06* (2013.01); *A61P 43/00* (2018.01)

(58) Field of Classification Search
CPC .................................................. C07D 401/06
See application file for complete search history.

(56) References Cited

U.S. PATENT DOCUMENTS

2006/0264408 A1* 11/2006 Haj-Yehia ............. A61K 31/60
                                                                    514/159

FOREIGN PATENT DOCUMENTS

WO    PCT/GB99/02218 A1    1/2000

OTHER PUBLICATIONS

Mancia, et al. 2007 Guidelines for the management of arterial hypertension. European Heart Journal (2007) 28, 1462-1536.
Haenni, et al. Treatment With a B-blocker With B2-Agonism Improves Glucose and Lipid Metabolism in Essential Hypertension. W. B. Saunders Company. Metabolism, vol. 43, No. 4 Apr. 1994: pp. 455-461.
Krespi, et al. Moxonidine Effect on Microalbuminuria, Thrombomodulin, and Plasminogen Activator Inhibitor-1 Levels in Patients with Essential Hypertension. Cardiovascular Drugs and Therapy 1998;12:463-467. Kluwer Academic Publishers. Boston, US.

* cited by examiner

Primary Examiner — Yong S. Chong
(74) Attorney, Agent, or Firm — Daniel M. Cohn; Howard M. Cohn

(57) ABSTRACT

Embodiments of the present invention generally concern pharmaceutical formulations and compositions and methods for using the pharmaceutical formulations and compositions which comprise derivatives of benzimidazole compounds, their racemic mixtures, their enantiomers, their complexes, their salts, and combinations thereof which have been found to be novel agonists of imidizoline receptors with surprising life extending efficacies due to their geroprotective (antigeriatric) actions on pathologies associated with the aging processes in humans and animals.

1 Claim, 3 Drawing Sheets

FIG. 1

TABLE 8: MLS of Fruit Flies As a Function of their Feed Being Exposed to a 1% Spray of Various Synthetic Benzimidazole Formula I Compounds

| Substance | Females | | Males | |
|---|---|---|---|---|
| | MLS (day) | EMLD (day) | MLS (day) | EMLD (day) |
| Control | 26±2 | 30.0 | 21±1 | 23.0 |
| IIIa | 35±5 | | 33±5 | |
| IIIb | 44±5 | | 42±6 | |
| IIIc | 32±6 | | 30±5 | |
| IIId | 37±5 | | 39±6 | |
| IIIe | 38±5 | | 36±5 | |
| IIIf | 32±5 | | 30±5 | |
| IIIg | 30±5 | | 30±5 | |
| IIIh | 52±5 | | 57±5 | |
| IIIi | 42±6 | | 42±6 | |
| Va | 40±5 | | 44±6 | |
| Vb | 33±5 | | 37±5 | |
| Vc | 37±5 | | 35±5 | |
| Vd | 43±6 | | 42±6 | |
| Ve | 40±5 | | 38±5 | |
| Vf | 43±5 | | 42±6 | |
| Vg | 44±6 | | 40±6 | |
| Vh | 43±5 | | 44±6 | |
| Vi | 32±5 | | 31±5 | |
| VIIa | 37±5 | | 34±5 | |
| VIIb | 38±5 | | 33±5 | |
| VIIc | 35±5 | | 38±5 | |
| VIId | 33±5 | | 37±5 | |
| VIIe | 30±5 | | 33±5 | |
| VIIf | 36±5 | | 37±5 | |

FIG. 2

TABLE 8 CONTINUED: MLS of Fruit Flies As a Function of their Feed Being Exposed a 1% Spray of Various Synthetic Benzimidazole Formula I Compounds

| Substance | Females | | Males | |
|---|---|---|---|---|
| | MLS (day) | EMLD (day) | MLS (day) | EMLD (day) |
| VIIg | 33±5 | | 39±5 | |
| VIIh | 39±5 | | 43±6 | |
| VIIi | 42±6 | | 48±7 | |
| IXa | 54±8 | | 59±8 | |
| IXb | 55±6 | | 57±8 | |
| IXc | 34±5 | | 42±5 | |
| IXd | 37±5 | | 36±5 | |
| IXe | 35±5 | | 38±5 | |
| IXf | 22±5 | | 26±5 | |
| IXg | 43±6 | | 44±6 | |
| XIa | 50±7 | | 57±7 | |
| XIb | 43±6 | | 44±6 | |
| XIc | 40±6 | | 42±6 | |
| XId | 33±5 | | 35±5 | |
| XIe | 36±5 | | 38±5 | |
| XIf | 37±5 | | 36±5 | |

FIG. 3

TABLE 8 CONTINUED: MLS of Fruit Flies As a Function of their Feed Being Exposed a 1% Spray of Various Synthetic Benzimidazole Formula I Compounds

| Substance | Females | | Males | |
|---|---|---|---|---|
| | MLS (day) | EMLD (day) | MLS (day) | EMLD (day) |
| XIg | 35±5 | | 39±5 | |
| XIh | 40±6 | | 44±6 | |
| XIi | 47±6 | | 48±7 | |
| XIIIa | 40±6 | | 38±5 | |
| XIIIb | 35±5 | | 35±5 | |
| XIIIc | 55±7 | | 59±7 | |
| XIIId | 44±6 | | 45±6 | |
| XIIIe | 40±5 | | 39±5 | |
| XIIIf | 45±6 | | 45±6 | |
| XIIIg | 32±5 | | 33±5 | |
| XIIIh | 54±8 | | 59±8 | |
| XIIIi | 43±6 | | 45±6 | |
| XVa | 49±7 | | 55±9 | |
| XVb | 47±6 | | 48±7 | |
| XVc | 45±6 | | 43±6 | |
| XVd | 49±8 | | 48±7 | |
| XVe | 44±6 | | 46±5 | |
| XVf | 40±5 | | 42±6 | |
| XVg | 67±9 | | 66±9 | |
| XVh | 55±8 | | 54±8 | |
| XVi | 50±8 | | 55±7 | |

DERIVATIZED BENZIMIDAZOLE COMPOUNDS, THEIR SALTS, THEIR COMPLEXES, THEIR PHARMACEUTICAL COMPOSITIONS AND METHODS FOR USING THEM FOR ANTIGERIATRIC ACTIONS

INVENTION FIELD

The invention relates to benzimidazole derivatives, their salts, and their pharmaceutical compositions useful in pharmacy, medicine and cosmetology for the prevention of and/or treatment of diseases associated with aging process.

BACKGROUND OF THE INVENTION

The emergence of selective agonists of $I_1$-imidazoline receptor has led to the class of centrally acting antihypertensive drugs (sympatholytics) in the treatment of arterial hypertension (AH). At the same time, the fact of the return of sympatholytics "second birth" to cardiological practice after a long break was officially recorded. Drugs in this group were among the first antihypertensive drugs that began to be used in clinical practice about 40 years ago, since in the pathogenesis of hypertension, the sympathetic nervous system was of great importance since the time of the neurogenic theory of G.F. Lang.

However, when it became clear that older generation sympatholytics (clonidine, methyldopa, reserpine) often cause serious side effects as drowsiness, depression, sexual dysfunction and the rebound phenomenon, they were no longer widely used as drugs for long-term antihypertensive therapy. They were used either for hypertensive crises or for economic reasons due to their relatively low cost. At the same time, the understanding of the importance of the sympathetic nervous system in the genesis of hypertension was so rooted in the consciousness of the medical community that research attempts to create new, effective, and safe sympatholytics has not stopped.

The relevance of the creation of such drugs increased even more when it became clear that the activation of the sympathetic nervous system leads to an increase in blood pressure (BP) and plays a role in the occurrence of a number of other negative effects, including metabolic disorders, which significantly increase the risk of complications in persons with hypertension. Among these effects, suffice it to mention myocardial hypertrophy, endothelial dysfunction, platelet activation, insulin resistance, and dyslipidemia. Thus, one of the most important areas of pharmacotherapy for hypertension is a multifaceted approach that decreases activity of the sympathoadrenal system, corrects metabolic disorders and assists in organ protection.

With the discovery of imidazoline receptors and the creation of its selective agonists, the emergence of new safe and effective sympatholytics has become realized. French scientists have located imidazoline receptors in the two most important organs regulating blood pressure, namely the brain and kidneys.

Imidazoline receptors are found in the lateral reticular nuclei of the rostral region of the medulla oblongata of the brain and in the proximal tubules of the kidneys. Imidazoline receptors do not react to catecholamines, but react to chemical compounds similar to imidazoline. Activation of imidazoline receptors in the brain causes a modulation of sympathetic impulses so as to decrease the blood pressure in an animal, and also effects the kidneys to decrease the activity of the tubular epithelial H+/Na+ exchange and to slow renal reabsorption of salt and water as a means for increasing urinary elimination of the salt and water.

Imidazoline Receptor Agonists

Agonists of imidazoline receptors (AIR), having a structure similar to imidazoline, and bind to these receptors in the brain and as a result reduce systemic sympathetic related activities. This results in a decrease in peripheral vascular resistance, a decrease in the activity of the renin-angiotensin system and a decrease in the renal reabsorption of salt and water. On the other hand, due to their relatively high binding affinity for imidazoline receptors, the agonists of imidazoline receptors in the therapeutic doses do not significantly affect adrenergic receptors, such as the α2 adrenergic receptors. By not affecting adrenergic receptors, therapeutic doses of AIR are associated with less adverse side effects and less frequently than other centrally acting drugs.

The side effects is associated with stimulation of the α2-adrenergic receptors, is the means by which both selective (α-methyldopa) and non-selective (clonidine) α2-adrenergic receptor agonists exercise their antihypertensive effect. Studies indicate that the antihypertensive efficacy of agonists of I-imidazoline receptor is comparable to the efficacy of the most potent and most used representatives of the main classes of antihypertensive drugs. The AIRs do not have a "slip away" effect or cause tolerance for the antihypertensive treatment. In addition, AIRs are well tolerated due to the fact, as mentioned above, that in therapeutic doses AIRs do not affect other adrenergic receptors. For these reasons the study of effects of AIR's metabolic effects is of particular interest.

The most convincing results were obtained in the studies of AIRs by Haenni A. et al. using the euglycemic clamp test method [Haenni, A., & Lithell, H. (1994). *Treatment with a β-blocker with β2-agonism improves glucose and lipid metabolism in essential hypertension. Metabolism*, 43(4), 455-461.]. Haenni found that the AIR compound known as moxonidine reduces insulin resistance. This study was conducted at the State Research Center for Preventive Medicine of Russian Federation and included studies of patients who have been diagnosed with mild to moderate hypertension and compensated diabetes mellitus type 2. The clinical studies found a positive effect of moxonidine on insulin resistance. For example, after 3 months of treatment with moxonidine, there was a significant decrease in insulin and blood glucose levels determined 2 hours after a standard breakfast (equivalent to a glucose tolerance test). These results indicate an improvement in tissue insulin sensitivity, due to less insulin required to maintain therapeutic glucose levels after moxonidine therapy.

A comparative randomized study called ALMAZ studied 202 patients with confirmed insulin resistance, and examined effects of moxonidine and metformin on glucose metabolism in patients with hypertension and with obesity. (See https://htn.almazovcentre.ru/jour/article/view/33?locale=en_US#). The ALMAZ study reported that moxonidine reduced fasting glucose levels, insulin resistance, patient weight, and also increased the rate of glucose utilization. The effect of these were on the glycemic profile in patients who are overweight, have mild hypertension, insulin resistance or impaired glucose tolerance was also evaluated. With moxonidine, fasting glucose decreased less than with metformin, but with both drugs the serum insulin levels decreased significantly, and the decrease in body mass index was similar. Interesting data was also obtained in the study on the simultaneous effect of imidazoline receptor agonists on sympathetic activity and metabolic parameters. The study focused on the efficacy of moxonidine, and included 41 patients with grade 1-3 hypertension (grade III risk).

In order to assess the activity of moxonidine on the patients before and after treatment of the sympathoadrenal system, a double dynamic test (DDT) for catecholamines (dopamine, norepinephrine, adrenaline) was performed in addition to the standard study of blood biochemical parameters (glycemic level, HbA1c, blood lipid spectrum). Also, leptin levels were examined in all patients. After 8 weeks of treatment with moxonidine, the achievement of the target BP level was accompanied by a significant decrease in the level of stress hormones, body mass index, insulin resistance and leptin concentration. It should also be noted that during treatment, a shift in the blood lipid spectrum towards anti-atherogenicity was recorded, specifically noted was a significant decrease in triglycerides and an increase in high-density lipoprotein cholesterol (HDL). Thus, the moxonidine administered in the form of the drug Moxogamma has been found to reproduce not only antihypertensive effects, but also demonstrated favorable metabolic effects and these effects together make Moxoogamma a modern, high-quality, generic drug.

Influence of Imidazoline Receptor Agonists on Endothelial Function

The ability of this group of drugs to improve endothelial function is considered to be significantly important clinically. Endothelial dysfunction is currently considered as a universal mechanism for the implementation of the atherogenic influence of various risk factors. Correction of endothelial dysfunction in addition to antihypertensive action can provide an effective reduction in the risk of cardiovascular complications in long-term therapy of hypertension. One of the indicators allowing an assessment of the functional status of the endothelium is the fibrinolytic activity of blood plasma. As is known, normal fibrinolytic activity is provided by a balance between levels tissue plasminogen activator (tPA) and its inhibitor (PAI-1), which are synthesized in endothelial cells. An increase in PAI-1 synthesis leads to a decrease in fibrinolytic activity, increasing the risk of progression of cardiovascular diseases. A significant decrease in the level of PAI-1 was found during therapy with moxonidine in patients with hypertension, and is hypothesized to be one of the possible mechanisms for a decrease in insulin resistance and the activity of the sympathoadrenal system (Krespi P G, Makris T K, Hatzizacharias A N, et al. *Moxonidine effect on microalbuminuria, thrombomodulin, and plasminogen activator inhibitor—1 levels in patients with essential hypertension. J Cardiovasc Drugs and Therapy* 1998; 12: 463-467.).

When the endothelium is damaged, there is found to also be decrease in the plasma level of thrombomodulin, a glycoprotein of membranes of endothelial cells, and this glycoprotein has a role as a receptor for thrombin and appears in blood plasma. Therefore, the decrease in thrombomodulin during therapy with moxonidine is probably associated with the maintenance of the integrity of the vascular endothelium. Thus, the results of recent studies have shown that selective agonists of $I_1$-imidazoline receptors provide not only adequate and long-term control of blood pressure, but also have a number of positive metabolic effects: a decrease in insulin resistance, increase in HDL cholesterol, improvement in endothelial function and improvement fibrinolytic activity of blood plasma. In the European guidelines of diagnosis and treatment of hypertension, AIR is assigned to the best class of drugs in terms of a beneficial effect on tissue sensitivity to insulin (2007 *Guidelines for the Management of Arterial Hypertension: The Task Force for the Management of Arterial Hypertension of the European Society of Hypertension (ESH) and of the European Society of Cardiology (ESC). J Hypertens* 2007; 25(6):1105-87.). In the Russian guidelines for the diagnosis and treatment of hypertension, the AIR niche is designated as the treatment of hypertension in combination with metabolic syndrome in combination with ACE inhibitors or angiotensin II receptor blockers. It is emphasized that these combinations not not only efficaciously reduce blood pressure, but also have a beneficial effect on target organs and reduce the risk of developing diabetes mellitus. Thus, the positive metabolic effects and organoprotection associated with AIR use on patients have received official recognition.

Agmatine as a High Affinity Ligand for Imidazoline Receptors

The hypothesis of the existence of imidazoline receptors was put forward by a group of researchers who studied the central hypotensive effect of the $I_2$-adrenergic receptor agonist clonidine which has an imidazoline group in its structure. Subsequently, in experiments on neurons in the rostral ventrolateral zone of the medulla oblongata (RVLM) of rats, evidence was obtained that at least 36% of specific binding sites in this zone differ from adrenergic ones and recognize imidazoline derivatives. Based on experiments with radio-ligands of different selectivity, the two main types of imidazoline receptors ($I_1$ and $I_2$) were identified. The $I_1$-receptors are marked with [3H]-clonidine and "recognize" all imidazoline and imidazole compounds, as well as oxazoline derivatives. The $I_2$-receptors have a high affinity for imidazoline derivatives (clonidine, moxonidine), medium affinity for imidazole derivatives (idazoxane, phentolamine) and low affinity for guanidine derivatives (amiloride, guanabenz). The $I_2$-receptors are involved in the implementation of the central antihypertensive effect of clonidine.

The $I_2$ receptors are labeled with [3H]-idazokean and recognize some imidazolines, benzodiazepines, and guanidine compounds. The $I_2$ receptors have a high affinity for imidazole and guanidine compounds, medium affinity for imidazole and new compounds. The $I_2$ receptors are divided into 2 subtypes: $I_{2a}$—with high and $I_{2b}$—with low affinity for amiloride. Recently, the classification of imidazoline receptors has been supplemented with $I_3$ receptors. The $I_3$ receptors have been found in the pancreas.

Imidazoline receptors of various types are localized in the central and peripheral nervous system, as well as in the heart, kidneys, stomach, pancreas, liver, large intestine, placenta, and prostate gland. The imidazoline receptors are involved in the reactions of the cardiovascular system, the regulation of intraocular pressure, the control of the secretion of hydrochloric acid in the stomach, the release of insulin, and the modulation of nociceptive responses. Imidazoline receptors have also been studied in connection with their possible participation in the development of pathological aging processes, such as depression, Alzheimer's disease, Parkinson's disease, and glial tumors.

The existence of imidazoline binding sites as a separate type of receptor suggested the presence of their endogenous ligand. In recent years, three main candidates for this role have been identified from animal tissues: the classical clonidine-substituted substance (cCDS), the immunoreactive clonidine-substituted substance (iCDS), and agmatine. Of the three candidates, the structure of the ligand for imidazoline receptors has been only determined for agmatine. Agmatine was isolated from the mammalian brain in 1994. is a decarboxylated arginine. Agmatine is decarboxylated arginine and Agmatine is formally named N-(4-aminobutyl) guanidine and its molecular structure is depicted below:

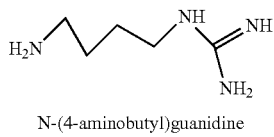

N-(4-aminobutyl)guanidine

Agmatine binds to imidazoline receptors of all subtypes in the concentration range of 0.5-5 mM. It is impossible to assert at present that agmatine is a selective endogenous ligand of imidazoline receptors due to its relatively low affinity and due to insufficient data on the effects of agmatine associated with action on these receptors.

Known compounds with activity against imidazoline receptors include the three-ring heterocyclic compounds known as carbolines which have a benzimidazole fragment. Some carboline structures are disclosed in patent application No. WO2000002878A1. Synthetic carbolines are hypothesized to be useful antihypertensive agents, neuroprotectors, nephroprotector and cardioprotectors. Inventors of the patent application WO2000002878A1 reported that some synthetic carbolines may have a greater than 100-fold affinity for $I_2$-receptors based on receptor modeling using benzodioxan receptor modeling compared to their affinity for adrenergic receptors modeling. An accumulation of some naturally occurring carbolines has been detected in rabbit brains. The synthetic carboline compounds disclosed in prior art patent application No. WO2000002878A1 are notably difficult to synthesize and furthermore they have not been reliably characterized in terms of their pharmacological biological activity. In addition, known carbolines lack a geroprotective action (prolongation of life span).

SUMMARY OF THE INVENTION

In some embodiments the present invention is a compound of Formula (1), a racemic mixture of the compound of the Formula (1), an enantiomer of the compound of the Formula (1), a salt of the compound of the Formula (1), a complex of the compound of the Formula (1), and any combination thereof, the compound of the Formula (1) comprising:

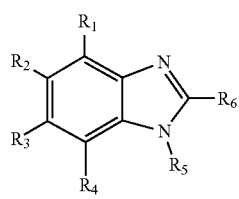

(1)

wherein substituents $R_1$, $R_2$, $R_3$, and $R_4$ are selected from the group consisting of H, $CH_3$, $C_2H_5$, Br, Cl, I, F, OH, CN, $NO_2$, COOH, and any combination thereof, wherein substituent $R_5$ selected from the group consisting of H, $CH_3$, and $C_2H_5$, wherein substituent $R_6$ is selected from the group consisting of

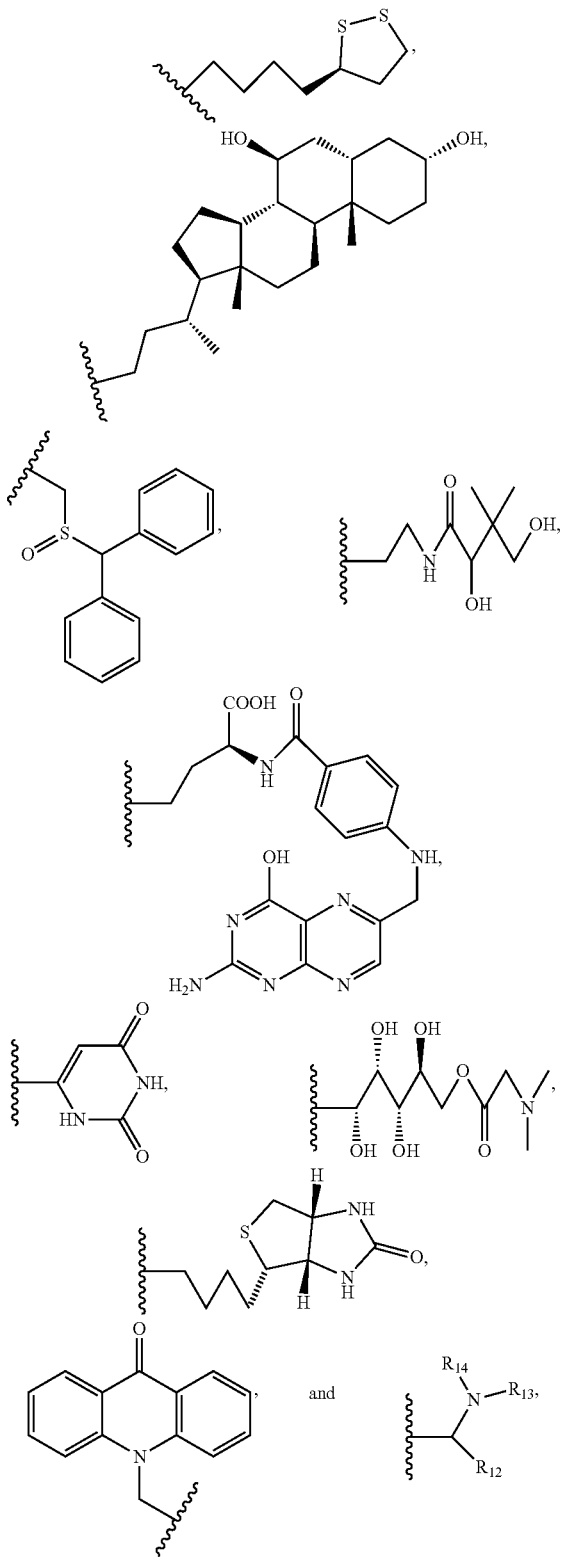

wherein substituents $R_{13}$ and $R_{14}$ are selected from the group consisting of H, $CH_3$, $C_2H_5$, and any combination thereof, wherein substituent $R_{12}$ is selected from the group consisting of $CH_3$,

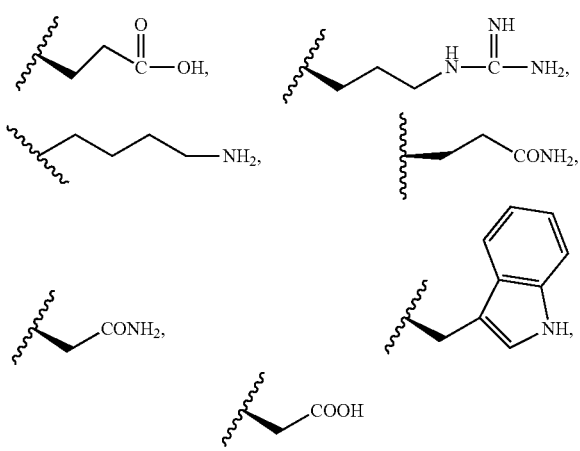

In some embodiments the present invention is a compound of Formula (1), a racemic mixture of the compound of the Formula (1), an enantiomer of the compound of the Formula (1), a salt of the compound of the Formula (1), a complex of the compound of the Formula (1), and any combination thereof, the compound of the Formula (1) comprising the salt selected from the group consisting of a hydrochloride, a hydrobromide, a hydroiodide, a sodium salt, a potassium salt, a lithium salt, a magnesium salt, a calcium salt, an iron salt, a copper salt, a zinc salt, an aluminum salt, a sulfate, a nitrate, a hydrogen phosphate, a phosphate, an acetate, a propionate, a hexanoate, cyclopentanepropionate, glycolate, a pyruvate, a lactate, malonate, a succinate, maliate, maleate, fumarate, tartrate, a citrate, benzoate, 3-(4-hydroxybenzoyl) benzoate, cinnaminate, mandelate, methanesulfonate, a besylate, an ethanesulfonate, 1,2-ethane-disulfonate, 2-hydroxyethanesulfonate, benzenesulfonate, 4-chlorobenzenesulfonate, 2-naphthalenesulfonate, 4-toluenesulfonate, camphorsulfonate, 4-methylbicyclo[2.2.2]-oct-2-ene-1-carboxylate, glucoheptonate, 3-phenylpropionate, trimethylacetate, tertiary butylacetate, lauryl sulfate, gluconate, glutamate, hydroxynaphthate, salicylate, stearate, muconate, a coordination complex with ethanolamine, a coordination complex with diethanolamine, a coordination complex with triethanolamine, a coordination complex with N-methylglucamine, a coordination complex with NTA, a coordination complex with HEPTA, a coordination complex with EGTA, a coordination complex with EDTA, a 2-napsylate, a 3-hydroxy-2-naphthoate, a 3-phenylpropionate, a 4-acetamidobenzoate, an acefyllinate, an aceturate, an adipate, an alginate, an aminosalicylate, an ammonium, an amsonate, an ascorbate, an aspartate, a bicarbonate, a bisulfate, a bitartrate, a borate, a butyrate, a calcium edetate, a camphocarbonate, a camphorate, a camsylate, a carbonate, a cholate, a clavulariate, a cyclopentane-propionate, a cypionate, a d-aspartate, a d-camsylate, a d-lactate, a decanoate, a dichloroacetate, a digluconate, a dodecylsulfate, an edisylate, an estolate, an esylate, an ethyl sulfate, a furate, a fusidate, a galactarate, a mucate, a galacturonate, a gallate, a gentisate, a gluceptate, a glucoheptanoate, a gluconate, a glucuronate, a glutamate, a glutarate, a glycerophosphate, a glycolate, a glycollylarsanilate, a hemisulfate, a heptanoate, an enanthate, a heptanoate, a hexafluorophosphate, a hexanoate, a hexylresorcinate, a hippurate, a hydrabenzate, a hydrabamine, a hydroxybenzoate, a hydroxynaphthoate, a chloride, a bromide, an iodide, a fluoride, an isethionate, an isothionate, an 1-aspartate, a 1-camsylate, an 1-lactate, a lactate, a lactobionate, a laurate, a laurylsulphonate, a meso-tartrate, a mesylate, a methanesulfonate, a methylbromide, a methylnitrate, a methylsulfate, a myristate, an N-methylglucamine an ammonium salt, a napadisilate, a naphthylate, a napsylate, a nicotinate, an octanoate, an oleate, an orotate, an oxalate, a palmitate, a pamoate, a pantothenate, a pectinate, a persulfate, a phenylpropionate, a phosphateldiphosphate, a picrate, a pivalate, a polygalacturonate, a pyrophosphate, a saccharate, a salicylsulfate, a subacetate, a sulfosaliculate, a sulfosalicylate, a suramate, a tannate, a teoclate, a terephthalate, a thiocyanate, a thiosalicylate, a tosylate, a tribrophenate, a triethiodide, an undecanoate, an undecylenate, a valerate, a valproate, a xinafoate, thioctic acid salt, a choline salt, a folate, and a combination thereof.

In some embodiments the present invention is a compound of Formula (1), a racemic mixture of the compound of the Formula (1), an enantiomer of the compound of the Formula (1), a salt of the compound of the Formula (1), a complex of the compound of the Formula (1), and any combination thereof, wherein the compound is the hydrochloride salt or is the thioctic acid salt.

In some embodiments the present invention is a compound of Formula (1), a racemic mixture of the compound of the Formula (1), an enantiomer of the compound of the Formula (1), a salt of the compound of the Formula (1), a complex of the compound of the Formula (1), and any combination thereof, wherein the compound is mixed with choline.

In some embodiments the present invention is a compound of Formula (1), a racemic mixture of the compound of the Formula (1), an enantiomer of the compound of the Formula (1), a salt of the compound of the Formula (1), a complex of the compound of the Formula (1), and any combination thereof, wherein the salt of the compound is the magnesium salt.

In some embodiments the present invention is a compound of Formula (1), a racemic mixture of the compound of the Formula (1), an enantiomer of the compound of the Formula (1), a salt of the compound of the Formula (1), a complex of the compound of the Formula (1), and any combination thereof, wherein the compound is in a complex with dapagliflozin.

In some embodiments the present invention is a compound of Formula (1), a racemic mixture of the compound of the Formula (1), an enantiomer of the compound of the Formula (1), a salt of the compound of the Formula (1), a complex of the compound of the Formula (1), and any combination thereof, wherein the compound is in a complex with 3-(1H-benzimidazol-2-yl)-1,2,2-trimethylcyclopentanecarboxylic acid.

In some embodiments the present invention is a compound of Formula (1), a racemic mixture of the compound of the Formula (1), an enantiomer of the compound of the Formula (1), a salt of the compound of the Formula (1), a complex of the compound of the Formula (1), and any combination thereof, wherein the compound is administered with metformin to a human or to an animal.

In some embodiments the present invention is a method of administering a dose of the compound of Formula (1), a racemic mixture of the compound of the Formula (1), an enantiomer, of the compound of the Formula (1), of a salt of the compound of the Formula (1), a complex of the compound of the Formula (1), and any combination thereof, in a pharmaceutical formulation by a route of administration as a means for using the compound to provide a medical treatment to a human or an animal.

In some embodiments the present invention is a method of administering a dose of the compound of Formula (1), a racemic mixture of the compound of the Formula (1), an enantiomer, of the compound of the Formula (1), of a salt of the compound of the Formula (1), a complex of the compound of the Formula (1), and any combination thereof, in a pharmaceutical formulation by a route of administration as a means for using the compound to provide a medical treatment to a human or an animal, wherein the dose of the compound is a milligram dose selected from the group consisting of about 0.05 mg to about 0.5 mg, about 0.5 mg to about 50 mg, about 50 mg to about 500 mg, about 500 mg to about 5,000 mg, and any combination thereof.

In some embodiments the present invention is a method of administering a dose of the compound of Formula (1), a racemic mixture of the compound of the Formula (1), an enantiomer, of the compound of the Formula (1), of a salt of the compound of the Formula (1), a complex of the compound of the Formula (1), and any combination thereof, in a pharmaceutical formulation by a route of administration as a means for using the compound to provide a medical treatment to a human or an animal, wherein the pharmaceutical formulation is selected from the group consisting of a parenteral pharmaceutical formulation, an injection solution pharmaceutical formulation, an injection suspension pharmaceutical formulation, a multiple dose vial pharmaceutical formulation, a compressed tablet pharmaceutical formulation, a coated tablet pharmaceutical formulation, a sugar-coated tablet pharmaceutical formulation, a soft gelatin capsule pharmaceutical formulation, a gelatin capsule pharmaceutical formulation, a pill pharmaceutical formulation, a cachet pharmaceutical formulation, a powder pharmaceutical formulation, a suppository pharmaceutical formulation, a rectal capsule pharmaceutical formulation, an oral solution pharmaceutical formulation, an oral suspension pharmaceutical formulation, a topical ointment pharmaceutical formulation, a topical crème pharmaceutical formulation, a topical liquid pharmaceutical formulation, an extended release pharmaceutical formulation, a slow release pharmaceutical formulation, a transdermal patch pharmaceutical formulation, a micronized aerosol pharmaceutical formulation for inhalation, an intravenous pharmaceutical formulation, a topical balm pharmaceutical formulation, a topical gel pharmaceutical formulation, and any combination thereof.

In some embodiments the present invention is a method of administering a dose of the compound of Formula (1), a racemic mixture of the compound of the Formula (1), an enantiomer, of the compound of the Formula (1), of a salt of the compound of the Formula (1), a complex of the compound of the Formula (1), and any combination thereof, in a pharmaceutical formulation by a route of administration as a means for using the compound to provide a medical treatment to a human or an animal, wherein the route of the administration is selected from the group consisting of a parenteral route, an intramuscular route, a subcutaneous route, an epidural route, an intracerebral route, a subthecal route, an intravenous route, a cardiac ventricular or atrial chamber route, a coronary artery route, a pulmonary route, a visceral cavity route, an oral route, a rectal route, an intrauterine cavity route, an intravaginal route, an intraurethral route, a sublingual route, a permucous route, an eye drop route, an intraocular route, an inhalation route, an in-dwelling cannula route, an arterial cannula route, a venous cannula route, an intranasal route, a transdermal route, and any combination thereof.

In some embodiments the present invention is a method of administering a dose of the compound of Formula (1), a racemic mixture of the compound of the Formula (1), an enantiomer, of the compound of the Formula (1), of a salt of the compound of the Formula (1), a complex of the compound of the Formula (1), and any combination thereof, in a pharmaceutical formulation by a route of administration as a means for using the compound to provide a medical treatment to a human or an animal, wherein the medical treatment to the human or the animal is selected from the group consisting of an cancer reducing treatment, a cancer prevention treatment, an anti-geriatric treatment, an anti-aging treatment, a kidney nephron protecting treatment, a cardiac muscle protecting treatment, an anti-arrhythmia treatment, a cardiac ischemia preventing treatment, a brain ischemia protecting treatment, a dementia treatment, a cerebroprotector treatment, a hepatoprotector treatment, an anti-hypertension treatment, a diabetes treatment, a diabetes preventing treatment, a body mass index lowering treatment, a tissue insulin sensitivity increasing treatment, an inflammatory disease reducing treatment, a preventative eye pathology treatment, a pregnancy eclampsia prevention treatment, an aerobic fitness improving treatment, a weight loss assisting treatment, a tissue ischemia preventing treatment, an organ ischemia preventing treatment, a tissue hypoxia preventing treatment, an organ hypoxia preventing treatment, an tissue edema preventing treatment, a cardiac hypertrophy pathology preventing treatment, a cardiac myopathy preventing treatment, a pituitary gland pathology preventing treatment, a pancreatic pathology preventing treatment, a thyroid pathology preventing treatment, and a combination thereof.

In some embodiments the present invention is a method of administering a dose of the compound of Formula (1), a racemic mixture of the compound of the Formula (1), an enantiomer, of the compound of the Formula (1), of a salt of the compound of the Formula (1), a complex of the compound of the Formula (1), and any combination thereof, in a pharmaceutical formulation by a route of administration as a means for using the compound to provide a medical treatment to a human or an animal, wherein the medical treatment to the human or the animal is for treating a pathology selected from the group consisting of a peripheral vascular resistance pathology, a renin-angiotensin system pathology, a salt and water retention pathology, and any combination thereof.

In some embodiments the present invention is a method of administering a dose of the compound of Formula (1), a racemic mixture of the compound of the Formula (1), an enantiomer, of the compound of the Formula (1), of a salt of the compound of the Formula (1), a complex of the compound of the Formula (1), and any combination thereof, in a pharmaceutical formulation by a route of administration as a means for using the compound to provide a medical treatment to a human or an animal, wherein the medical treatment to the human or the animal is for treating a pathology selected the group consisting of the pathology arising from a radiation treatment to the human or the animal, the pathology arising from a chemotherapy treatment to the human or the animal, the pathology arising from an immunotherapy treatment to the human or the animal, the pathology arising from the human or the animal having cancer, the pathology arising from the human or the animal having a test to detect a cancer presence, the pathology arising from the human or the animal having an adverse reaction to a biopsy sample taken from them, and any combination thereof.

In some embodiments the present invention is a method of administering a dose of the compound of Formula (1), a racemic mixture of the compound of the Formula (1), an enantiomer, of the compound of the Formula (1), of a salt of the compound of the Formula (1), a complex of the compound of the Formula (1), and any combination thereof, in a pharmaceutical formulation by a route of administration as a means for using the compound to provide a medical treatment to a human or an animal, wherein the medical treatment to the human or the animal is selected from the group consisting of a reducing wrinkling of the skin treatment, a reducing hair loss treatment, a plastic surgery tissue treatment, a reducing wound scaring treatment, an improving wound healing treatment, an increasing a tissue blood circulation treatment, an increasing an organ blood circulation treatment, an improving a muscle tone treatment, a reducing a fat accumulation treatment, and any combination thereof.

In some embodiments the present invention is a method of administering a dose of the compound of Formula (1), a racemic mixture of the compound of the Formula (1), an enantiomer, of the compound of the Formula (1), of a salt of the compound of the Formula (1), a complex of the compound of the Formula (1), and any combination thereof, in a pharmaceutical formulation by a route of administration as a means for using the compound to provide a medical treatment to a human or an animal, wherein the dose of the compound administered is used for treating a pathology caused by an aging of the body of the human or the animal, and wherein the treating of the pathology is related to activating imidazoline receptors in the body of the human or the animal.

In some embodiments the present invention is a method of administering a dose of the compound of Formula (1), a racemic mixture of the compound of the Formula (1), an enantiomer, of the compound of the Formula (1), of a salt of the compound of the Formula (1), a complex of the compound of the Formula (1), and any combination thereof, in a pharmaceutical formulation by a route of administration as a means for using the compound to provide a medical treatment to a human or an animal, wherein the dose of the compound administered is used for causing a measureable therapeutic effect to the human or the animal, and wherein the measureable therapeutic effect can be measured by a test conducted at a hospital, a medical clinic, by a medical doctor, or by a blood analysis test laboratory.

In some embodiments the present invention is an anti-geriatic compound of Formula (1), a racemic mixture of the compound of the Formula (1), an enantiomer, a salt of the compound of the Formula (1), a complex of the compound of the Formula (1), and any combination thereof, wherein the compound of Formula (1) is selected from the group consisting of the compounds IIIa, IIIb, IIIc, IIId, IIIe, IIIf, IIIg, IIIh, III, Va, Vb, Vc, Vd, Ve, Vf, Vg, Vh, Vi, VIIa, VIIb, VIIc, VIId, VIIe, VIIf, VIIg, VIIh, VIIi, IXa, IXb, IXc, IXd, IXe, IXf, IXg, Xia, XIb, XIc, XId, XIe, XIf, XIg, XIh, Xii, XIIIa, XIIIb, XIIIc, XIIId, XIIIe, XIIIf, XIIIg, XIIIh, XIIIi, XVa, XVb, XVc, XVd, XVe, XVf, XVg, XVh, and XVi.

20. In some embodiments the present invention is an anti-geriatric compound of Formula (1), a racemic mixture of the compound of the Formula (1), an enantiomer, a salt of the compound of the Formula (1), a complex of the compound of the Formula (1), and any combination thereof, with wherein the compound of Formula (1) is selected from the group consisting of the compounds IIIh, IXa, IXb, Xia, XIIIh, XVa, XVg, XVh, and XVi.

BRIEF DESCRIPTION OF THE DRAWINGS

FIG. 1. provides the scheme of Synthesis of Claim 1 Compound Derivatives (III)

FIG. 2. provides the scheme of Synthesis of Claim 1 Compound Derivatives (V)

FIG. 3. provides the scheme of Synthesis of Claim 1 Compound Derivatives (VII)

FIG. 4. provides the scheme of Synthesis of Claim 1 Compound Derivatives (IX)

FIG. 5. provides the scheme of Synthesis of Claim 1 Compound Derivatives (XI)

FIG. 6. provides the scheme of Synthesis of Claim 1 Compound Derivatives (XIII)

FIG. 7. provides the scheme of Synthesis of Claim 1 Compound Derivatives (XV)

FIG. 8. provides a first portion of a Table 8 which tabulates the median life span (MLS) that is geroprotective effect of present invention imidazoline receptor activator compounds which are also termed in the specification as synthetic Benzimidazole Formula 1 compounds of the invention Nos. IIIa-VIIf). The relative geroprotective effectiveness (efficacy, action) each of these compounds is determined by each compounds effect on the median lifespan of fruit flies which have been genetically selected to inherently possess a substantially reduced lifespan. Each Formula 1 compound was dosed to the flied in the form of a 1 percent solution sprayed into the feed of the fruit flies. There is also control fruit fly data.

FIG. 9 provides a middle portion of a Table 8 which tabulates the median life span (MLS) that is geroprotective effect of present invention imidazoline receptor activator compounds which are also termed in the specification as synthetic Benzimidazole Formula 1 compounds of the invention Nos. VIIg-XIIIe). The relative geroprotective effectiveness (efficacy, action) each of these compounds is determined by each compounds effect on the median lifespan of fruit flies which have been genetically selected to inherently possess a substantially reduced lifespan. Each Formula 1 compound was dosed to the flied in the form of a 1 percent solution sprayed into the feed of the fruit flies. There is also control fruit fly data.

FIG. 10 provides the end portion of a Table 8 which tabulates the median life span (MLS) that is geroprotective effect of present invention imidazoline receptor activator compounds which are also termed in the specification as synthetic Benzimidazole Formula 1 compounds Nos. XIIIf-XVi). The relative geroprotective effectiveness (efficacy, action) each of these compounds is determined by each compounds effect on the median lifespan of fruit flies which have been genetically selected to inherently possess a substantially reduced lifespan. Each Formula 1 compound was dosed to the flied in the form of a 1 percent solution sprayed into the feed of the fruit flies. There is also control fruit fly data.

DETAILED DESCRIPTION OF THE INVENTION

It is an important objective of some embodiments of the present invention to provide compounds which are new and effective derivatives of benzimidazole, their racemic mixtures, theire enantiomers, their complexes, their salts, and a combination thereof wherein the compounds exhibit anti-geriatric actions, the compounds comprising the below Formula 1 Structure:

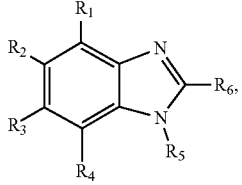
(1)

wherein substituent $R_{1-4}$ is selected from the group consisting of H, $CH_3$, $C_2H_5$, Br, Cl, I, F, OH, CN, $NO_2$, and COOH, wherein substituent $R_5$ is selected from the group consisting of H, $CH_3$, and $C_2H_5$, wherein substituent $R_6$ has a chemical structure selected from the group consisting of

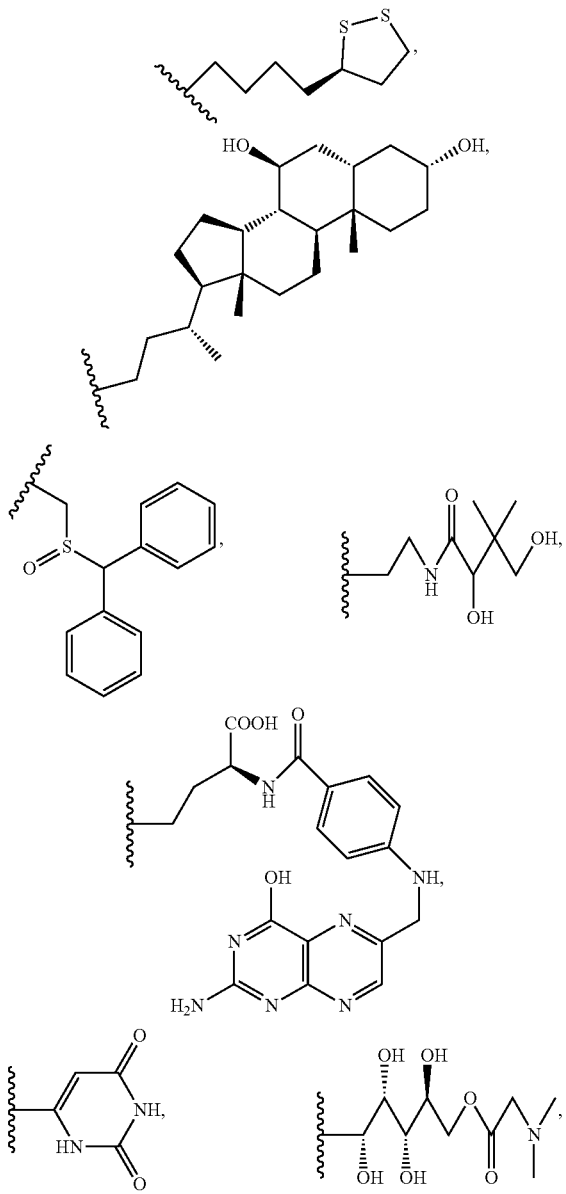

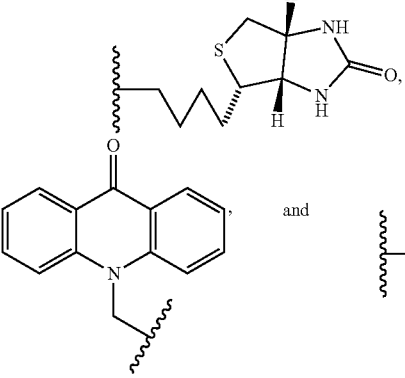

and wherein substituent $R_{13,14}$ is selected from the group consisting of H, $CH_3$, and $C_2H_5$, and wherein substituent $R_{12}$ is selected from the group consisting of $CH_3$,

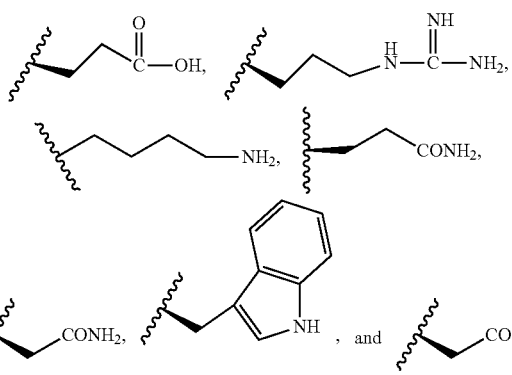

The present invention includes embodiments which are a salt of a Formula 1 compound. Example salts of a Formula 1 compound include a salt selected from the group consisting hydrochloride salts, hydrobromide salt, hydroiodide salt, sodium salt, potassium salt, magnesium salt, calcium salt, iron salt, and a copper salt. Additional examples of Formula 1 compounds and their salts their combination as a pharmaceutical formulation including a compound selected from the group consisting of thioctic acid, metformin, choline, dapagliflozin, and a complex with 3-(1H-benzimidazol-2-yl)-1,2,2-trimethylcyclopentanecarboxylic acid. Complexes and salts of the Formula 1 compounds are useful for manufacturing drugs including AIRs which are selective activators and/or agonists of imidazoline receptors for the treatment of pathologies caused by aging.

Based on these structures, an effective dose amount of pharmaceutical compositions of the Formula 1 compounds, salts, complexes and combinations of chemical substance named above, optionally formulated with one or more pharmaceutically acceptable excipients, are particularly useful therapeutic compositions for administration to a person as a method of treating one or more pathologies associated with or believed to be caused by an aging of the body of the person, Some effective dose amounts are an effective amount of between about 0.05 mg to 10,000 mg, preferably between about 0.5 mg to about 1,000 mg.

Separately, the composition may contain, as a mixture, thioctic acid, metformin, choline, dapagliflozin, 3-(1H-benzimidazol-2-yl)-1,2,2-trimethylcyclopentane carboxylic acid alone or in a mixture with each other. Said pharmaceutical compositions can be used in various dosage forms as a pharmaceutical formulation which is selected from the group consisting of a parenteral formulation, an injection solution, an injection suspension, a multiple dose vial formulation, a plain tablet, a coated tablet, a sugar-coated tablet, a plate capsule, a gel capsule, a pill, a cachet, a powder, a suppository, a rectal capsule, an oral solutions, an oral suspensions, a topical ointment, a transdermal patch, a micronized aerosol formulation for inhalation, an intravenous formulation, a topical formulation, and a topical gel.

The pharmaceutical compositions of the present invention in some embodiments are administered by a route selected from the group consisting of parenteral, intramuscular, intracerebral, intravenous, intracardiac, oral, rectal, permucous, eye drop, inhalation, in-dwelling cannula, coronary cannula, arterial cannula, venous cannula, intranasal, and transdermal. The uses of some embodiments of the present invention are designed as pharmaceutical drugs for the treatment of pathologies by the aging process as drugs functioning as therapeutic agents selected from the group consisting of anticancer agents, life prolongation agents, nephroprotector agents, cardioprotector agents, cerebroprotector agents, hepatoprotector agents, antihypertensive agents, as agents that increase the sensitivity of tissues to insulin, and a combination thereof.

Example 1: Synthesis of Formula 1 Compound Derivatives (III)

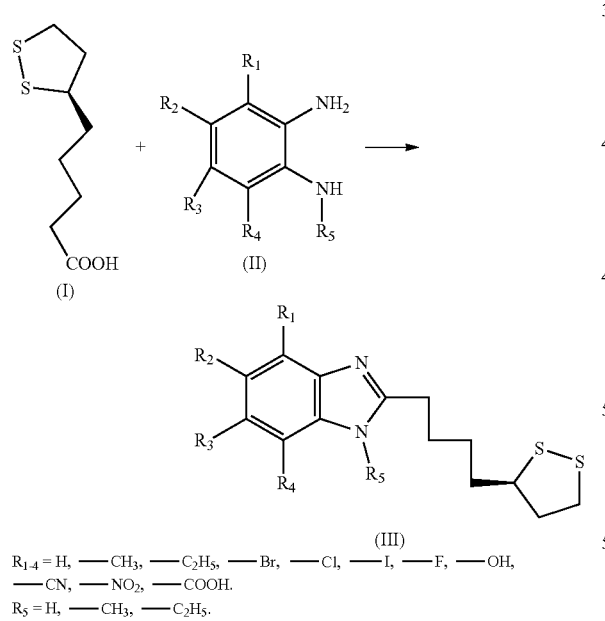

FIG. 1. Scheme of Synthesis of Claim 1 Compound Derivatives (III)

A mixture of 2.05 g (0.01 mole) of thioctic acid (I), 1.08 g of 0.01 mole) substituted ortho-phenylenediamine (I, 15 ml of glacial acetic acid and 5 ml of dimethylformamide was boiled for 60 minutes. The solution was cooled, the formed precipitate (Ill) is filtered off and dried, and then crystallized from ethanol. The yield was 70-85%.

Instead of unsubstituted (II), its substituted derivatives can be made with $R_{1-4}$ as H, $CH_3$, $C_2H_5$, Br, Cl, I, F, OH, CN, $NO_2$, or COOH and with $R_5$ as H, $CH_3$, $C_2H_5$, or I.

Instead of glacial acetic acid, a mixture of 1.5 ml of toluene and 5 ml of dimethylformamide can be used. Instead of recrystallization, precipitation from a solution of glacial acetic acid with isopropyl alcohol can be used by adding 5 ml of isopropyl alcohol to the cooled reaction mixture and settling the solution for a day. The precipitate that formed can be filtered off and reprecipitated from glacial acetic acid with isopropanol as described above. Table 1 below tabulates the analysis data for some of the synthesized Formula 1 Compound Derivatives ($I_1$).

TABLE 1

Results of NMR $^{13}$C Analysis of some of the Synthesized Formula 1 Compound Derivatives (III) and their Percent (%) Synthesis Yields:

| Substance Code | Substituents | NMR $^{13}$C, PPM | % Yield Theoretical |
|---|---|---|---|
| IIIa | $R_{1-5}$ = H | 56.3(CH); 38.5($CH_2$); 138.9(C); 151.4(C); 40.2($CH_2$); 115.2(CH); 123.0(CH); 34.9($CH_2$); 29.2($CH_2$); 25.2($CH_2$); 22.1($CH_2$) | 85 ± 10 |
| IIIb | $R_{1-3,5}$ = H, and $R_4$ = COOH | 56.3(CH); 38.5($CH_2$); 138.9(C); 151.4(C); 129.5(C); 138.8(C); 40.2($CH_2$); 125.6(CH) 120.4(CH); 122.9(CH) 166.4(C);; 34.9($CH_2$); 29.2($CH_2$); 25.2($CH_2$); 22.1($CH_2$) | 77 ± 10 |
| IIIc | $R_{1,3-5}$ = H, and $R_2$ = $NO_2$ | 56.3(CH); 38.5($CH_2$); 151.4(C); 142.5(C); 138.7(C); 40.2($CH_2$); 144.3(C); 112.9(CH); 116.1(CH); 118.6(CH); 34.9($CH_2$); 29.2($CH_2$); 25.2($CH_2$); 22.1($CH_2$) | 80 ± 10 |
| IIId | $R_{1,3,5}$ = H, and $R_{2,4}$ = $CH_3$ | 56.3(CH); 38.5($CH_2$); 151.4(C); 138.7(C); 135.4(C); 40.2($CH_2$); 126.1(C); 112.3 (CH); 132.6(C); 124.3(CH); 29.2($CH_2$); 16.5($CH_3$); 21.6($CH_3$); 25.2 ($CH_2$); 22.1($CH_2$) | 79 ± 10 |
| IIIe | $R_{1,3,5}$ = H, and $R_{2,4}$ = Br | 56.3(CH); 38.5($CH_2$); 148.2(C); 128.8(C); 119.4(CH); 40.2($CH_2$); 122.3(C); 127.9(CH); 34.9($CH_2$); 28.8($CH_2$); 136.9(CH); 116.1($CH_2$); 25.2($CH_2$); 22.1($CH_2$) | 80 ± 10 |
| IIIe | $R_{1,3,5}$ = H, and $R_{2,4}$ = Cl | 56.3(CH); 38.5($CH_2$); 151.4(C); 141.7(C); 136.4(CH); 40.2($CH_2$); 122.1(C); 130.6 (C); 113.9(CH); 123.7(CH); 34.9($CH_2$); 29.2($CH_2$); 25.2($CH_2$); 22.1($CH_2$) | 85 ± 10 |
| IIIf | $R_{1,3}$ = H, and $R_{2,4,5}$ = $CH_3$ | 56.3(CH); 38.5($CH_2$); 151.4(C); 153.0(C); 138.7(C); 135.6(C); 40.2($CH_2$); 126.1(C); 112.3(CH); 132.6(C); 124.3(CH); 32.3($CH_3$); 34.9($CH_2$); 26.7($CH_2$); 16.8($CH_3$); 21.6($CH_3$); 25.2($CH_2$); 22.4($CH_2$) | 75 ± 10 |
| IIIg | $R_{1,2,4}$ = H, $R_3$ = F, and $R_5$ = $C_2H_5$ | 56.3(CH); 38.5($CH_2$); 154.7(C); 137.8(C); 135.8(C); 40.2($CH_2$); 156.5(C); 102.4(CH); 116.8(CH); 109.9(CH); 40.4($CH_2$); 34.9($CH_2$); 27.0($CH_2$); 25.2($CH_2$); 22.4($CH_2$); 15.1($CH_3$) | 80 ± 10 |
| IIIh | $R_{1,4}$ = H, $R_3$ = I, $R_2$ =OH, and $R_5$ = I | 56.3(CH); 38.5($CH_2$); 141.5(C); 132.1(C); 139.2(C); 40.2($CH_2$); 78.9(C); 160.6(C); 125.7(CH); 104.0(CH); 34.9($CH_2$); 27.7($CH_2$); 25.2($CH_2$); 21.2($CH_2$) | 85 ± 10 |

Example 2: Synthesis of Formula 1 Compound Derivatives (V)

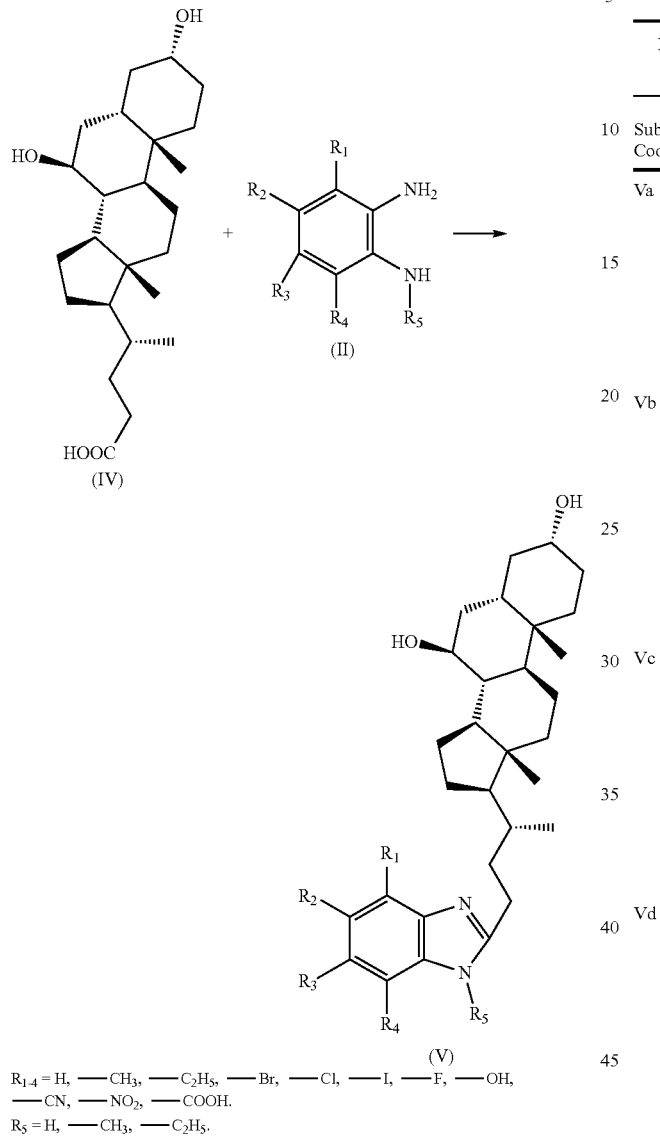

R$_{1-4}$ = H, —CH$_3$, —C$_2$H$_5$, —Br, —Cl, —I, —F, —OH, —CN, —NO$_2$, —COOH.
R$_5$ = H, —CH$_3$, —C$_2$H$_5$.

FIG. 2. Scheme of Synthesis of Claim 1 Compound Derivatives (V)

A mixture of 3.9 g (0.01 mole) ursodeoxycholic acid (IV), 1.08 g (0.01 mole) ortho-phenylenediamine (I), 10 ml of glacial acetic acid and 3 ml of dimethylformamide was boiled for 90 minutes. The solution was cooled, the formed precipitate (V) was filtered off and dried, and then was crystallized from methanol. The yield was 70-85%.

Instead of unsubstituted (H), its substituted derivatives can be made with R$_{1-4}$ as MH, CH$_3$, C$_2$H$_5$, Br, Cl, I, F, OH, CN, NO$_2$, or COOH, and with R$_5$ as H, CH$_3$, C$_2$H$_5$, or I.

Instead of glacial acetic acid, a mixture of 9 ml of toluene and 9 ml of dimethylformamide can be used. Instead of recrystallization, precipitation from a solution of glacial acetic acid with isopropyl alcohol can be used by adding 5 ml of water to the cooled reaction mixture and settling the solution for a day. The precipitate that formed is filtered off can be re-precipitated from glacial acetic acid with water as described above. Table 2 below tabulates the analysis data for some of the synthesized Formula 1 Compound Derivatives (V).

TABLE 2

Results of $^{13}$C NMR Analysis of some of the Synthesized Formula 1 Compound Derivatives (V) and their Percent (%) Synthesis Yield Percentages

| Substance Code | Substituents | NMR $^{13}$C, PPM | % Yield Theoretical |
|---|---|---|---|
| Va | R$_{1-5}$ = H | 151.4(C); 139.9(C); 138.9(C); 43.0(C); 50.4(CH); 56.3(CH); 24.5(CH$_2$); 28.3(CH$_2$); 68.4(CH); 71.4(CH); 115.2(CH); 40.0(CH); 40.2(CH$_2$); 123.0(CH); 35.8(C); 41.9(CH); 41.1(CH); 37.4(CH); 30.9(CH$_2$); 21.0(CH$_2$); 35.6(CH$_2$); 35.4(CH); 27.0(CH$_2$); 13.6(CH$_3$); 38.9(CH$_2$); 19.3(CH$_3$) | 60 ± 10 |
| Vb | R$_{1-3,5}$ = H, and R$_4$ = COOH | 151.4(C); 138.8(C); 129.5(C); 43.0(C); 50.4(CH); 56.3(CH); 24.5(CH$_2$); 28.3(CH$_2$); 68.4(CH); 71.4(CH); 117.5(CH); 120.4(CH); 40.0(CH); 40.2(CH$_2$); 125.6(CH); 122.9(CH); 35.8(C); 41.9(CH); 41.1(CH); 37.4(CH); 30.9(CH$_2$); 21.0(CH$_2$); 35.6(CH$_2$); 166.4(C); 35.40(CH); 27.0(CH$_2$); 13.6(CH$_3$); 38.9(CH$_2$); 19.4(CH$_3$) | 52 ± 10 |
| Vc | R$_{1,3-5}$ = H, and R$_2$ = NO$_2$ | 151.4(C); 139.8(C); 135.4(C); 43.0(C); 50.4(CH); 56.3(CH); 24.5(CH$_2$); 28.3(CH$_2$); 68.4(CH); 71.4(CH); 126.1(C); 112.3(CH); 40.0(CH); 40.2(CH$_2$); 118.6(CH); 123.9(CH); 35.8(C); 41.9(CH); 41.1(CH); 37.4(CH); 30.9(CH$_2$); 21.0(CH$_2$); 35.6(CH$_2$); 35.40(CH); 27.0(CH$_2$); 13.6(CH$_3$); 38.9(CH$_2$); 19.4(CH$_3$) | 55 ± 10 |
| Vd | R$_{1,3,5}$ = H, and R$_{2,4}$ = CH$_3$ | 151.4(C); 138.7(C); 133.7(C); 43.0(C); 50.4(CH); 56.3(CH); 24.5(CH$_2$); 28.3(CH$_2$); 68.4(CH); 71.4(CH); 137.0(C); 121.3(CH); 40.0(CH); 40.2(CH$_2$); 132.6(C); 124.3(CH); 35.8(C); 41.9(CH); 41.1(CH); 37.4(CH); 30.9(CH$_2$); 21.0(CH$_2$); 35.6(CH$_2$); 35.40(CH); 27.0(CH$_2$); 13.6(CH$_3$); 16.5(CH$_3$); 21.6(CH$_3$); 13.5(CH$_3$); 38.9(CH$_2$); 19.4(CH$_3$) | 50 ± 10 |
| Ve | R$_{1,3,5}$ = H, And R$_{2,4}$ = Cl | 151.4(C); 141.7(C); 136.4(C); 43.0(C); 50.4(CH); 56.3(CH); 24.5(CH$_2$); 28.3(CH$_2$); 122.1(C); 130.6(C); 68.4(CH); 71.4(CH); 113.9(CH); 40.0(CH); 40.2(CH$_2$); 123.7(CH); 35.8(C); 41.9(CH); 41.1(CH); 37.4(CH); 30.9(CH$_2$); 21.0(CH$_2$); 35.6(CH$_2$); 35.40(CH); 27.0(CH$_2$); 13.6(CH$_3$); 13.5(CH$_3$); 38.9(CH$_2$); 19.4(CH$_3$) | 45 ± 10 |
| Ve | R$_{1,3,5}$ = H, and R$_{2,4}$ = Br | 151.4(C); 143.3(C); 140.2(C); 43.0(C); 50.4(CH); 56.3(CH); 24.5(CH$_2$); 28.3(CH$_2$); 112.2(C); 119.7(C); 68.4(CH); 71.4(CH); 117.7(CH); 40.0(CH); 40.2(CH$_2$); 129.5(CH); 35.8(C); 41.9(CH); 41.1(CH); 37.4(CH$_2$); 30.9(CH$_2$); 21.0(CH$_2$); 35.6(CH$_2$); 35.40(CH); | 60 ± 10 |

TABLE 2-continued

Results of $^{13}$C NMR Analysis of some of the Synthesized Formula 1 Compound Derivatives (V) and their Percent (%) Synthesis Yield Percentages

| Substance Code | Substituents | NMR $^{13}$C, PPM | % Yield Theoretical |
|---|---|---|---|
| Vf | $R_{1,3}$ = H, and $R_{2,4,5}$ = $CH_3$ | 27.0($CH_2$); 13.6($CH_3$); 38.9($CH_2$); 19.4($CH_3$) 153.0(C); 138.7(C); 135.6(C); 43.0(C); 50.4(CH); 56.3(CH); 24.5($CH_2$); 28.3($CH_2$); 68.4(CH); 71.4(CH); 126.1(C); 112.3(CH); 40.0(CH); 40.2($CH_2$); 132.6(C); 124.3(CH); 35.8(C); 41.9(CH); 41.1(CH); 37.4($CH_2$); 30.9($CH_2$); 21.0($CH_2$); 35.6($CH_2$); 32.3($CH_3$); 35.4(CH); 24.5($CH_2$); 13.6($CH_3$); 16.8($CH_3$); 21.6($CH_3$); 13.5($CH_3$); 39.2($CH_2$); 19.4($CH_3$) | 65 ± 10 |
| Vg | $R_{1,2,4}$ = H, $R_3$ = F, and $R_5$ = $C_2H_5$ | 154.7(C); 137.8(C); 135.8(C); 43.0(C); 50.4(CH); 56.3(CH); 24.5($CH_2$); 28.3($CH_2$); 156.5(C); 68.4(CH); 71.4(CH); 102.3(CH); 116.8(CH); 40.0(CH); 40.2($CH_2$); 109.9(CH); 35.8(C); 41.9(CH); 41.1(CH); 37.4($CH_2$); 30.9($CH_2$); 21.0($CH_2$); 35.6($CH_2$); 40.4($CH_2$); 35.4(CH); 24.8($CH_2$); 13.6($CH_3$); 39.2($CH_2$); 15.1($CH_3$); 19.4($CH_3$) | 50 ± 10 |
| Vh | $R_{1,4}$ = H, $R_3$ = I, $R_2$ = OH; and $R_5$ = I | 141.5(C); 132.0(C); 139.2(C); 43.0(C); 50.4(CH); 56.3(CH); 24.5($CH_2$); 28.3($CH_2$); 78.9(C); 160.6(C); 68.4(CH); 71.4(CH); 125.7(CH); 104.0(CH); 40.0(CH); 40.2($CH_2$); 35.8(C); 41.9(CH); 41.9(CH); 41.1(CH); 37.4($CH_2$); 30.9($CH_2$); 21.0($CH_2$); 35.6($CH_2$); 35.4(CH); 25.5($CH_2$); 13.5($CH_3$); 38.0($CH_2$); 19.4($CH_3$) | 55 ± 10 |

Example 3. Synthesis of Derivative (VII)

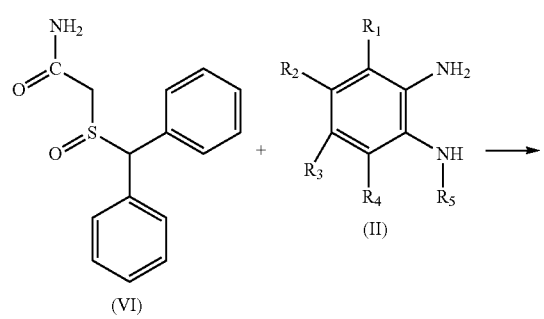

(VI) + (II)

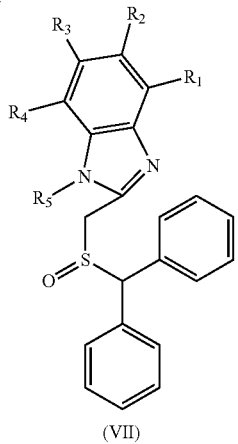

(VII)

$R_{1-4}$ = H, —$CH_3$, —$C_2H_5$, —Br, —Cl, —I, —F, —OH, —CN, —$NO_2$, —COOH.
$R_5$ = H, —$CH_3$, —$C_2H_5$.

FIG. 3. Scheme of Synthesis of Claim 1 Compound Derivatives (VII)

A mixture of 2.7 g (0.01 mole) of modafinil (VI), 1.08 g (0.01 mole) of ortho-phenylenediamine (II), 5 ml of glacial acetic acid and 3 ml of dimethylformamide was boiled for 90 minutes. The solution was cooled, the precipitate (VII) formed was filtered off and dried and then crystallized from methanol. The yield was 60-65%.

Instead of unsubstituted (II), its substituted derivatives can be made with $R_{1-4}$ as H, $CH_3$, $C_2H_5$, Br, Cl, I, F, OH, CN, $NO_2$, or COOH and with $R_5$ as H, $CH_3$, $C_2H_5$, or I.

Instead of glacial acetic acid, a mixture of 5 ml of toluene and 5 ml of dimethylformamide can be used. Instead of recrystallization, precipitation from a solution of glacial acetic acid can be used by adding 5 ml of water to the cooled reaction mixture and settling the solution for a day. The precipitate that forms can be filtered off and re-precipitated from glacial acetic acid with water as described above.

Table 3 below tabulates the analysis data for some of the synthesized Formula 1 Compound Derivatives (VII).

TABLE 3

Results of NMR $^{13}$C Analysis of some of Synthesized Formula 1 Compounds (VII) and Percentage (%) Synthesis Yields

| Substance Code | Substituents | NMR $^{13}$C, PPM | % Yield Theoretical |
|---|---|---|---|
| VIIa | $R_{1-5}$ = H | 141.5 (C); 138.9 (C); 115.2 (CH); 135.2 (CH); 123.1 (CH); 130.0 (CH); 129.2 (CH); 126.2 (CH); 49.8 ($CH_2$); 67.2 (CH) | 63 ± 10 |
| VIIb | $R_{1-3,5}$ = H, and $R_4$ = COOH | 141.5 (C); 138.8 (C); 129.5 (C); 117.5 (C); 120.4 (CH); 135.2 (C); 125.6 (CH); 122.9 (CH); 130.1 (CH); 129.2 (CH); 126.2 (CH); 49.8 ($CH_2$) | 67 ± 10 |
| VIIc | $R_{1,3-5}$ = H, and R= $NO_2$ | 141.5 (C); 145.0 (C); 144.3 (C); 112.9 (CH); 116.1 (CH); 135.2 (C); 118.6 (CH); 130.1 (CH); 129.2 (CH); 126.2 (CH); 49.8 ($CH_2$) | 55 ± 10 |
| VIId | $R_{1,3-5}$ = H, and $R_{2,4}$ = $CH_3$ | 141.5 (C); 138.7 (C); 135.4 (C); 126.1 (C); 112.3 (CH); 132.6 (C); 135.2 (C); 124.3 (CH); 130.1 (CH); 129.2 (CH); 126.2 (CH); 49.8 (CH2) | 50 ± 10 |

TABLE 3-continued

Results of NMR $^{13}$C Analysis of some of Synthesized Formula 1 Compounds (VII) and Percentage (%) Synthesis Yields

| Substance Code | Substituents | NMR $^{13}$C, PPM | % Yield Theoretical |
|---|---|---|---|
| VIIe | $R_{1,3-5}$ = H, and $R_{2,4}$ = Cl | 141.5 (C); 141.7 (C); 136.4 (C); 122.1 (C); 130.6 (C); 113.9 (CH); 135.2 (C); 123.7 (CH); 130.1 (CH); 129.2 (CH); 126.2 (CH); 49.8 (CH$_2$); 67.2 (CH); | 66 ± 10 |
| VIIf | $R_{1,3-5}$ = H, and $R_{2,4}$ = Br | 141.5 (C); 143.3 (C); 140.2 (C); 112.1 (C); 119.7 (C); 117.7 (CH); 135.2 (C); 129.5 (CH); 130.1 (CH); 129.2 (CH); 126.2 (CH); 49.8 (CH$_2$); 67.2 (CH); | 60 ± 10 |
| VIIg | $R_{1,3}$ = H, and $R_{2,4,5}$ = CH$_3$ | 141.5 (C); 138.7 (C); 135.6 (C); 126.1 (C); 112.3 (CH); 132.6 (C); 135.2 (C); 124.3 (CH); 130.1 (CH); 129.2 (CH); 126.2 (CH); 47.3 (CH$_2$); 67.2 (CH); 32.5 (CH$_3$); 16.8 (CH$_3$); 21.6 (CH$_3$); | 72 ± 10 |
| VIIh | $R_{1,2,4}$ = H, $R_3$ = F, and $R_5$ = C$_2$H$_5$ | 141.5 (C); 137.8 (C); 135.8 (C); 156.5 (C); 102.4 (CH); 116.8 (CH); 135.2 (C); 109.9 (CH); 130.1 (CH); 129.2 (CH); 126.2 (CH); 47.6 (CH$_2$); 67.2 (CH); 40.6 (CH$_2$); 15.1 (CH$_3$) | 58 ± 10 |
| VIIi | $R_{1,4}$ = H, $R_3$ = I, $R_2$ = OH and $R_5$ = I | 141.5 (C); 132.1 (C); 139.2 (C); 78.9 (C); 160.6 (C); 125.7 (CH); 104.0 (CH); 135.2 (C); 109.9 (CH); 130.1 (CH); 129.2 (CH); 126.2 (CH); 48.3 (CH$_2$); 67.2 (CH) | 55 ± 10 |

Example 4. Synthesis of Derivative (IX)

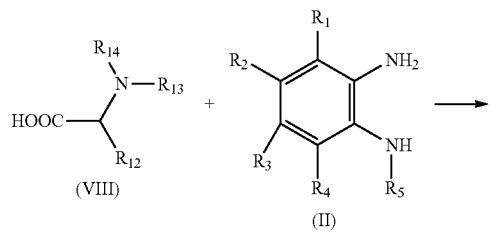

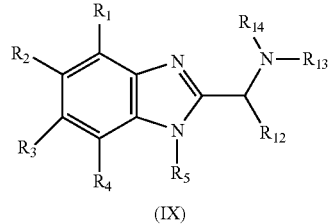

(IX)

$R_{1-4}$ = H, —CH$_3$, —C$_2$H$_5$, —Br, —Cl, —I, —F, —OH, —CN, —NO$_2$, —COOH;
$R_5$ = H, —CH$_3$, —C$_2$H$_5$;
$R_{12}$ = —CH$_3$;
$R_{13,14}$ = H, —CH$_3$, —C$_2$H$_5$;

FIG. 4. Scheme of Synthesis of Claim 1 Compound Derivatives (IX)

A mixture of 0.01 mole of amino acid (VIII), 0.01 mole of ortho-phenylenediamine (II), 10 ml of glacial acetic acid was boiled for 60 minutes. The solution was cooled, 7 ml of isopropyl alcohol was added, a day later the precipitate (IX) was filtered off and dried and then was re-precipitated from glacial acetic acid with isopropanol as described above. The yield was 70-85%.

Instead of unsubstituted (II), its substituted derivatives can be made with $R_{1-4}$ as H, CH$_3$, C$_2$H$_5$, Br, Cl, I, F, OH, CN, NO$_2$, or COOH, and with $R_5$ as H, CH$_3$, C$_2$H$_5$, or I. The amino acid (VIII) can be selected for example, as an unsubstituted or a substituted derivative of an amino acid such as for example glutamic acid, aspartic acid, arginine, lysine, an amide of glutamic, an amide of aspartic acid, valine, tryptophan, or alanine.

Instead of glacial acetic acid, a mixture of 5 ml of toluene and 5 ml of dimethylformamide can be used. Instead of recrystallization, precipitation from a solution of glacial acetic acid can be used by adding 5 ml of water to the cooled reaction mixture and settling the solution for a day. The precipitate that forms can be filtered off and reprecipitated from glacial acetic acid with water as described above. Table 4 below tabulates the analysis data for some of the synthesized Formula I Compounds (IX).

TABLE 4

Results of NMR $^{13}$C Analysis of some of Synthesized Formula I Compounds (IX) and Percentage (%) Synthesis Yields

| Substance Code | Substituents | | NMR $^{13}$C, PPM | % Yield Theoretical |
|---|---|---|---|---|
| IXa | $R_{1-5,13,14}$ = H, and $R_{12}$ = (propyl-NH-C(=NH)-NH$_2$ group) | | 141.5 (C); 138.9 (C); 115.2 (CH); 123.0 (CH); 158.0 (CH); 55.1 (CH); 41.9 (CH); 36.5 (CH); 24.8 (CH$_2$) | 65 ± 10 |
| IXb | $R_{1-5,13,14}$ = H, and $R_{12}$ = (butyl-NH$_2$ group) | | 141.5 (C); 138.9 (C); 115.2 (CH); 123.0 (CH); 158.0 (CH); 55.1 (CH); 42.0 (CH); 36.5 (CH); 27.2 (CH$_2$) | 60 ± 10 |

TABLE 4-continued

Results of NMR $^{13}$C Analysis of some of Synthesized Formula I Compounds (IX) and Percentage (%) Synthesis Yields

| Substance Code | Substituents | NMR $^{13}$C, PPM | % Yield Theoretical |
|---|---|---|---|
| IXc | $R_{1-5,13,14}$ = H, and $R_{11}$ = 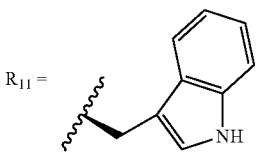 | 141.5 (C); 138.9 (C); 136.5 (CH); 123.0 (CH); 127.4 (C); 110.8 (C); 115.2 (CH); 111.2 (CH); 118.8 (CH); 123.0 (CH); 121.7 (CH); 119.8 (CH); 58.6 (CH); 37.8 (CH$_2$) | 75 ± 10 |
| IXd | $R_{1-5,13,14}$ = H, and $R_{12}$ = 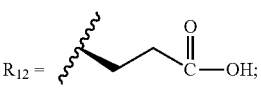 | 141.5 (C); 138.9 (C); 115.2 (CH); 123.0 (CH); 178.4 (C); 54.8 (CH); 30.6 (CH); 33.0 (CH$_2$) | 79 ± 10 |
| IXe | $R_{1-5,13,14}$ = H, and $R_{12}$ =  | 141.5 (C); 138.9 (C); 115.2 (CH); 123.0 (CH); 172.1 (C); 50.2 (CH); 44.8 (CH$_2$) | 66 ± 10 |
| IXf | $R_{1-5,13,14}$ = H, and $R_{12}$ = 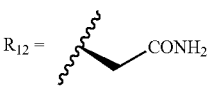 | 141.5 (C); 138.9 (C); 115.2 (CH); 123.0 (CH); 174.3 (C); 50.8 (CH); 46.4 (CH$_2$) | 80 ± 10 |
| IXg | $R_{1-5,13,14}$ = H, and $R_{12}$ = 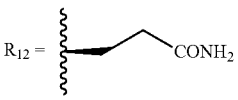 | 141.5 (C); 138.9 (C); 115.2 (CH); 123.0 (CH); 74.3 (CH$_2$); 55.4 (CH); 21.6 (CH$_2$); 35.4 (CH$_2$) | 75 ± 10 |

Example 5. Synthesis of Derivative (XI)

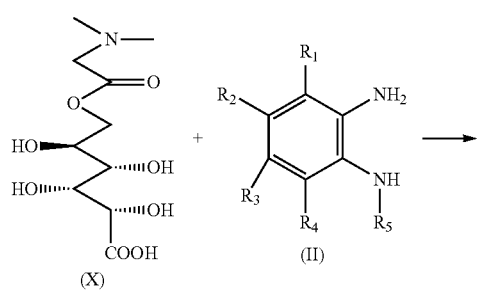

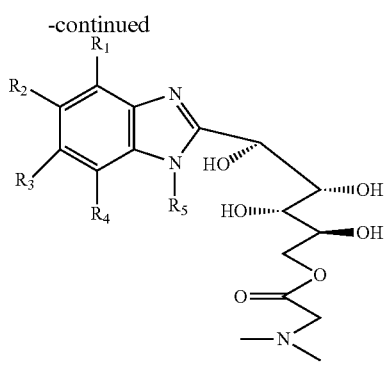

$R_{1-4}$ = H, —CH$_3$, —C$_2$H$_5$, —Br, —Cl, —I, —F, —OH, —CN, —NO$_2$, —COOH;
$R_5$ = H, —CH$_3$, —C$_2$H$_5$;

FIG. 5. Scheme of Synthesis of Claim 1 Compound Derivatives (XI) A mixture of 0.01 mole of pangamic acid (X), 0.01 mole of ortho-phenylenediamine (II), 10 ml of glacial acetic acid was boiled for 30 minutes. The solution was cooled, 5 ml of isopropyl alcohol was added, a day later the precipitate (XI) was filtered off and dried, and then was re-precipitated from glacial acetic acid with isopropanol as described above. The yield was 60-75%.

Instead of unsubstituted (II), its substituted derivatives can be made with $R_{1-4}$ as H, $CH_3$, $C_2H_5$, Br, Cl, I, F, OH, CN, $NO_2$, or COOH, and with $R_5$ as H, $CH_3$, $C_2H_5$, or I. Instead of pangamic acid (X), alternatively, biotin, pantothenic acid, folic acid, cyanocobalamin can be used.

Instead of glacial acetic acid, a mixture of 5 ml of toluene and 5 ml of dimethylformamide can be used. To purify the product, precipitation from a solution of glacial acetic acid can be used by adding 5 ml of water to the cooled reaction mixture and settling the solution for a day. The precipitate that formed is filtered off and reprecipitated from glacial acetic acid with water as described above. Table 5 below tabulates the analysis data for some of the synthesized Formula I Compounds (XI).

TABLE 5

Results of NMR $^{13}$C Analysis of some of Synthesized Formula 1 Compounds (XI) and Percentage (%) Synthesis Yields

| Substance Code | Substituents | NMR $^{13}$C, PPM | % Yield Theoretical |
|---|---|---|---|
| XIa | $R_{1-5}$ = H | 141.5 (C); 138.9 (C); 115.2 (CH); 123.1 (CH); 171.2 (C); 66.9 (CH); 70.3 (CH); 69.1 (CH); 69.3 (CH); 65.0 ($CH_2$); 47.2 ($CH_2$); 53.9 ($CH_3$) | 63 ± 10 |
| XIb | $R_{1-3,5}$ = H, and $R_4$ = COOH | 141.5 (C); 138.8 (C); 117.5 (C); 120.4 (CH); 125.6 (CH); 122.9 (CH); 166.4 (C); 171.2 (C); 66.9 (CH); 70.3 (CH); 69.1 (CH); 69.3 (CH); 65.0 ($CH_2$); 47.2 ($CH_2$); 53.9 ($CH_3$) | 60 ± 10 |
| XIc | $R_{1,3-5}$ = H, and $R_2$ = $NO_2$ | 141.5 (C); 139.8 (C); 133.7 (C); 137.0 (C); 121.3 (CH); 118.6 (CH); 123.9 (CH); 171.2 (C); 66.9 (CH); 70.3 (CH); 69.1 (CH); 69.3 (CH); 65.0 ($CH_2$); 47.2 ($CH_2$); 53.9 ($CH_3$) | 75 ± 10 |
| XId | $R_{1,3,5}$ = H, and $R_{2,4}$ = —$CH_3$ | 141.5 (C); 138.7 (C); 135.4 (C); 126.1 (C); 112.3 (CH); 132.6 (C); 124.3 (CH); 171.2 (C); 66.9 (CH); 70.3 (CH); 69.1 (CH); 69.3 (CH); 65.0 ($CH_2$); 47.2 ($CH_2$); 53.9 ($CH_3$); 16.5 ($CH_3$); 21.6 ($CH_3$) | 50 ± 10 |
| XIe | $R_{1,3,5}$ = H, and $R_{2,4}$ = Cl | 141.5 (C); 141.7 (C); 136.4 (C); 122.1 (CH); 130.6 (CH); 113.9 (CH); 135.2 (C); 123.7 (CH); 130.1 (CH); 129.2 (CH); 126.2 (CH); 49.8 ($CH_2$); 67.2 (CH); | 66 ± 10 |
| XIf | $R_{1,3,5}$ = H, and $R_{2,4}$ = Br | 141.5 (C); 143.3 (C); 140.2 (C); 112.1 (C); 119.7 (C); 117.7 (CH); 135.2 (C); 129.5 (CH); 130.1 (CH); 129.2 (CH); 126.2 (CH); 49.8 ($CH_2$); 67.2 (CH); | 60 ± 10 |
| XIg | $R_{1,3}$ = H, and $R_{2,4,5}$ = $CH_3$ | 141.5 (C); 138.7 (C); 135.6 (C); 126.1 (C); 112.3 (CH); 132.6 (C); 135.2 (C); 124.3 (CH); 130.1 (CH); 129.2 (CH); 126.2 (CH); 47.3 ($CH_2$); 67.2 ($CH_2$); 32.5 ($CH_3$); 16.8 ($CH_3$); 21.6 ($CH_3$) | 72 ± 10 |
| XIh | $R_{1,2,4}$ = H, $R_3$ = F, and $R_5$ = $C_2H_5$ | 141.5 (C); 137.8 (C); 135.8 (C); 156.5 (C); 102.4 (CH); 116.8 (CH); 135.2 (C); 109.9 (CH); 130.1 (CH); 129.2 (CH); 126.2 (CH); 47.6 ($CH_2$); 67.2 (CH); 40.6 ($CH_2$); 15.1 ($CH_3$) | 58 ± 10 |
| XIi | $R_{1,4}$ = H, $R_3$ = I, $R_2$ = OH, and $R_5$ = I | 141.5 (C); 132.1 (C); 139.2 (C); 78.9 (C); 160.6 (C); 125.7 (CH); 104.0 (CH); 135.2 (CH); 109.9 (CH); 130.1 (CH); 129.2 (CH); 126.2 (CH); 48.3 ($CH_2$); 67.2 (CH) | 55 ± 10 |

Example 6. Synthesis of Derivative (XIII)

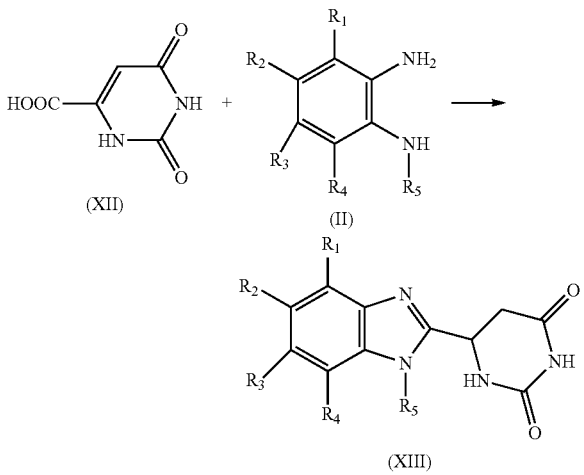

(XIII)

$R_{1-4}$ = H, —$CH_3$, —$C_2H_5$, —Br, —Cl, —I, —F, —OH, —CN, —$NO_2$, —COOH;
$R_5$ = H, —$CH_3$, —$C_2H_5$;

FIG. 6. Scheme of Synthesis of Claim 1 Compound Derivatives (XIII)

A mixture of 0.01 mole of orotic acid (XII), 0.01 mole of ortho-phenylenediamine (II), 10 ml of glacial acetic acid was boiled for 90 minutes. The solution was cooled, 5 ml of isopropyl alcohol was added, after a day the precipitate (XIII) was filtered off and dried, and then was re-precipitated from glacial acetic acid with isopropanol as described above. The yield was 65-75%.

Instead of unsubstituted (II), its substituted derivatives can be made with $R_{1-4}$ as H, $CH_3$, $C_2H_5$, Br, Cl, I, F, OH, CN, $NO_2$, or COOH, and with $R_5$ as H, $CH_3$, $C_2H_5$, or I.

Instead of glacial acetic acid, a mixture of 5 ml of toluene and 5 ml of dimethylformamide can be used. To purify the product, precipitation from a solution of glacial acetic acid can be used by adding 5 ml of water to the cooled reaction mixture and settling the solution for a day. The precipitate that formed is filtered off and reprecipitated from glacial acetic acid with water as described above. Table 6 below tabulates the analysis data of some of the synthesized Formula I Compounds (XIII).

TABLE 5

Results of NMR $^{13}$C Analysis of some of Synthesized Formula 1 Compounds (XIII) and Percentage (%) Synthesis Yields

| Substance Code | Substituents | NMR $^{13}$C, PPM | % Yield Theoretical |
|---|---|---|---|
| XIIIa | $R_{1-5}$ = H | 141.5 (C); 138.9 (C); 150.7 (CH); 163.5 (CH); 154.7 (CH); 115.2 (CH); 95.3 (CH); 123.0 (CH) | 65 ± 10 |
| XIIIb | $R_{1-3,5}$ = H, and $R_4$ = COOH | 141.5 (C); 138.8 (C); 129.5 (C); 150.7 (C); 163.5 (C); 154.7 (C); 117.5 (C); 120.4 (CH); 95.3 (CH); 125.6 (CH); 122.9 (CH); 166.4 (C) | 75 ± 10 |
| XIIIc | $R_{1,3-5}$ = H, and $R_2$ = $NO_2$ | 141.5 (C); 139.8 (C); 133.7 (C); 150.7 (C); 163.5 (C); 154.7 (C); 137.0 (C); 121.3 (CH); 95.3 (CH); 118.6 (CH); 123.9 (CH) | 75 ± 10 |

TABLE 5-continued

Results of NMR $^{13}$C Analysis of some of Synthesized Formula 1 Compounds (XIII) and Percentage (%) Synthesis Yields

| Substance Code | Substituents | NMR $^{13}$C, PPM | % Yield Theoretical |
|---|---|---|---|
| XIIId | $R_{1,3,5}$ = H, and $R_{2,4}$ = $CH_3$ | 141.5 (C); 138.7 (C); 135.4 (C); 150.7 (C); 163.5 (C); 154.7 (C); 126.1 (C); 112.3 (CH); 132.6 (C); 95.3 (CH); 124.3 (CH); 16.5 (CH$_3$); 21.6 (CH$_3$) | 80 ± 10 |
| XIIIe | $R_{1,3,5}$ = H, and $R_{2,4}$ = Cl | 141.5 (C); 141.7 (C); 136.4 (C); 122.1 (C); 130.6 (C); 150.7 (C); 163.5 (C); 154.7 (C); 113.9 (CH); 123.7 (CH); 95.3 (CH) | 78 ± 10 |
| XIIIf | $R_{1,3,5}$ = H, and $R_{2,4}$ = Br | 141.5 (C); 143.3 (C); 140.2 (C); 112.1 (C); 119.7 (C); 150.7 (CH); 163.5 (C); 154.7 (C); 117.7 (CH); 129.2 (CH); 95.3 (CH) | 60 ± 10 |
| XIIIg | $R_{1,3}$ = H, and $R_{2,4,5}$ = $CH_3$ | 141.5 (C); 138.7 (C); 135.6 (C); 150.7 (C); 163.5 (C); 154.7 (C); 126.1 (C); 112.3 (CH); 132.6 (CH); 95.3 (CH); 124.3 (CH); 34.4 (CH$_3$); 16.8 (CH$_3$); 21.6 (CH$_3$) | 80 ± 10 |
| XIIIh | $R_{1,2,4}$ = H, $R_3$ = F, and $R_5$ = $C_2H_5$ | 141.5 (C); 134.5 (C); 135.8 (C); 156.5 (C); 150.7 (CH); 163.5 (CH); 154.7 (C); 102.4 (CH); 116.8 (CH); 95.3 (CH); 109.9 (CH); 40.5 (CH$_2$); 15.2 (CH$_3$) | 58 ± 10 |
| XIIIi | $R_{1,4}$ = H, $R_3$ = I, $R_2$ = OH, and $R_5$ = I | 141.5 (C); 132.1 (C); 139.2 (C); 78.9 (C); 150.7 (CH); 163.5 (CH); 160.6 (CH); 154.7 (C); 125.7 (CH); 104.0 (CH); 95.3 (CH) | 55 ± 10 |

Example 7. Synthesis of Derivative (XIV)

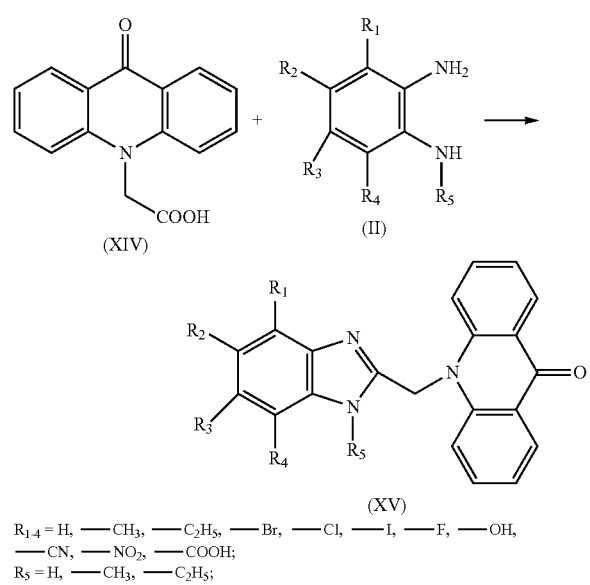

FIG. 7. Scheme of Synthesis of Claim 1 Compound Derivatives (XV)

A mixture of 0.01 mole of acridoneacetic acid (XIV), 0.01 mole of ortho-phenylenediamine (II), 10 ml of glacial acetic acid was boiled for 90 minutes. The solution was cooled, 5 ml of isopropyl alcohol was added, after a day the precipitate (XV) was filtered off and dried, and then re-precipitated from glacial acetic acid with isopropanol as described above. The yield was 55-60%.

Instead of unsubstituted (II), its substituted derivatives can be made with $R_{1-4}$ as H, $CH_3$, $C_2H_5$, Br, Cl, I, F, OH, CN, $NO_2$, or COOH, and with $R_5$ as H, $CH_3$, $C_2H_5$, or I.

Instead of glacial acetic acid, a mixture of 5 ml of toluene and 5 ml of dimethylformamide can be used. To purify the product, precipitation from a solution of glacial acetic acid can be used by adding 5 ml of water to the cooled reaction mixture and settling the solution for a day. The precipitate that formed is filtered off and reprecipitated from glacial acetic acid with water as described above. Table 7 below tabulates the analysis data of some of the synthesized Formula I Compounds (XV).

TABLE 7

Results of NMR $^{13}$C Analysis of some of Synthesized Formula 1 Compounds (XV) and Percentage (%) Synthesis Yields

| Substance Code | Substituents | NMR $^{13}$C, PPM | % Yield Theoretical |
|---|---|---|---|
| XVa | $R_{1-5}$ = H | 141.5 (C); 138.9 (C); 175.7 (C); 144.4 (C); 115.2 (CH); 121.7 (C); 116.2 (CH); 123.0 (CH); 126.5 (CH); 133.3 (CH); 121.5 (CH); 61.4 (CH$_2$) | 57 ± 3 |
| XVb | $R_{1-3,5}$ = H, and $R_4$ = COOH | 141.5 (C); 138.9 (C); 129.5 (C); 175.7 (C); 144.4 (C); 117.5 (CH); 120.4 (C); 121.7 (C); 116.2 (CH); 125.6 (CH); 122.9 (CH); 126.5 (CH); 133.3 (CH); 121.5 (CH); 166.4 (C); 61.4 (CH$_2$) | 52 ± 10 |
| XVc | $R_{1,3-5}$ = H, and $R_2$ = $NO_2$ | 141.5 (C); 142.5 (C); 145.0 (C); 144.4 (C); 112.9 (CH); 121.7 (C); 116.1 (CH); 121.7 (C); 116.2 (CH); 118.6 (CH); 126.5 (CH); 133.3 (CH); 121.5 (CH); 61.4 (CH$_2$) | 55 ± 5 |
| XVd | $R_{1,3,5}$ = H, and $R_{2,4}$ = $CH_3$ | 141.5 (C); 141.7 (C); 136.4 (C); 122.1 (C); 130.6 (C); 175.7 (C); 144.4 (C); 113.9 (CH); 121.7 (C); 123.7 (CH); 116.2 (CH); 126.5 (CH); 133.3 (CH); 121.5 (CH); 61.4 (CH$_2$) | 60 ± 10 |
| XVe | $R_{1,3,5}$ = H, and $R_{2,4}$ = Cl | 141.5 (C); 141.7 (C); 136.4 (C); 122.1 (C); 130.6 (C); 150.7 (C); 163.5 (C); 154.7 (CH); 113.9 (CH); 123.7 (CH); 95.3 (CH) | 70 ± 10 |
| XVf | $R_{1,3,5}$ = H, and $R_{2,4}$ = Br | 141.5 (C); 143.3 (C); 140.2 (C); 112.2 (C); 119.7 (C); 175.7 (C); 144.4 (C); 117.7 (CH); 121.7 (C); 129.5 (CH); 116.2 (CH); 126.5 (CH); 133.3 (CH); 121.5 (CH); 61.4 (CH$_2$) | 55 ± 10 |
| XVg | $R_{1,3}$ = H, and $R_{2,4,5}$ = $CH_3$ | 148.1 (C); 138.7 (C); 135.6 (C); 175.7 (C); 144.4 (C); 126.1 (C); 112.3 (CH$_3$); 121.7 (C); 132.6 (CH); 116.2 (CH); 124.3 (CH); 126.5 (CH); 133.3 (CH); 121.5 (CH); 32.0 (CH$_3$); 16.8 (CH$_3$); 21.6 (CH$_3$); 58.9 (CH$_2$) | 65 ± 10 |
| XVh | $R_{1,2,4}$ = H, $R_3$ = F, and $R_5$ = $C_2H_5$ | 148.1 (C); 137.8 (C); 135.8 (C); 156.54 (C); 175.7 (C); 144.4 (C); 102.4 (CH); 116.8 (CH); 121.7 (C); 116.2 (CH); 109.9 (CH); 126.5 (CH); 116.3 (CH); | 55 ± 10 |

TABLE 7-continued

Results of NMR $^{13}$C Analysis of some of Synthesized Formula 1 Compounds (XV) and Percentage (%) Synthesis Yields

| Substance Code | Substituents | NMR $^{13}$C, PPM | % Yield Theoretical |
|---|---|---|---|
| XVi | $R_{1,4}$ = H, $R_3$ = I, $R_2$ = OH, and $R_5$ = I | 126.5 (CH); 133.3 (CH); 121.5 (CH); 40.0 (CH$_2$); 59.2 (CH$_2$); 15.1 (CH$_3$) 141.5 (C); 132.1 (C); 139.2 (C); 78.9 (C); 175.7 (C); 160.6 (C); 144.4 (C); 125.7 (CH); 104.0 (CH); 121.7 (C); 116.2 (CH); 126.5 (CH); 116.2 (CH); 126.5 (CH); 133.3 (CH); 121.5 (CH); 59.9 (CH$_2$) | 50 ± 10 |

Example 8: Geroprotective Activity of the Synthesized Formula I Compounds

An important effect of imidazoline receptor activators is a geroprotective effect (an increase in the lifespan of animals). For the present invention the term animal shall mean any kind of animal, such as a pet, a human, a patient, a living subject, or a person.

One well-studied animal-lifespan model for the inventors has been the survival model of the insect Drosophila (fruit fly) due to their relatively short lifespan. Drosophila melanogaster lines were selected for their differences in reproductive function. The genetic selection of related Drosophila lines was been carried out for reproductive function (sexual activity of males). The genetic selection was accomplished by close inbreeding with individual crosses in each generation of full brothers and sisters. Using this process of genetic selection, a series of fruit fly lines differing in breeding characteristics (BA−, HA−, HA+) were repeatedly obtained by a method of return genetic selection. This selection process led to an acquisition of low-level fruit fly lines with a complex number of genetically-controlled changes. The most interesting genetically-controlled changes affected the neuroendocrine system of the flies and this became the subject of special studies by the inventors. In the Drosophila lines laid down from the natural population of "GL", the genetic selection was carried out to select for fruit fly embryonic mortality accompanied by close inbreeding.

As a result of the special studies, two contrasting inbred lines were obtained for further study. The two contrasting inbred lines are: (1) a high (HEM line) and (2) a low embryonic mortality (LEM line). At the same time, a sample of flies from the natural population of the GL was maintained as a Control fruit flies group without any genetic selection in mass fruit fly crops. It was found that the fruit fly lines of HEM and GL are characterized by having a threefold difference in their number of viable offspring, while not differing in fertility which was determined by the number of laid eggs per unit of time. In the HEM line, 81% of fruit fly eggs stopped developing at early stages of ontogenesis. The HEM line was found to have a high frequency of an early dominant lethal (EDL) mortality which increased from 65% on the first day of fruit fly egg laying to 95% on the fourth day of the fruit fly egg laying. No differences were found between the two studied lines in terms of late dominant lethality. Further genetic analysis determined that the frequency and the dynamics of the occurrence of early dominant lethal (EDL) in the high embryonic mortality (HEM) fruit fly line was only determined by the genotype of the female flies. In addition, a system of balanced lethal mutations arose in the HEM line by the 86th generation of directed selection which was found to create a permanent heterozygosity on a small section of the second chromosome of the fruit flies.

Terminology Related to the Present Invention

Antigeriatric action is an action which includes pharmacological effects aimed at prolonging the life of a living organism: these drugs include histone deacetylase inhibitors, phosphodiesterase inhibitors, type $I_1$ and $I_2$ imidazoline receptor stimulants, activators of telomerase expression, immunomodulators, antiviral agents, anticancer agents, statins, and antihyperglycemic drugs (metformin). A common generic feature of this pharmacological action is ae physical extension of human or animal life.

Telomerase is an enzyme that adds specific repeating DNA sequences (TTAGGG in vertebrates) to the 3'-end of the DNA strand in telomere regions that are located at the ends of chromosomes in eukaryotic cells. Telomeres contain condensed DNA and stabilize chromosomes. With each cell division, the telomeric regions are shortened. The existence of a mechanism that compensates for the shortening of telomeres (telomerase) was predicted in 1973 by A. M. Olovnikov. Telomerase is a reverse transcriptase, and a special RNA molecule is associated with it, which is used as a template for reverse transcription during telomere elongation.

As a result of the telomerase activity, the length of telomeric regions of the cell's chromosomes increases or remains at a constant level, thus compensating for terminal under replication and allowing the cell to divide for an unlimited time. In the course of the study of this enzyme (consisting, as described below, of the RNA component and the protein component), it was found that the RNA component is expressed at a constant level in almost all cells, and the expression of the protein component is required to induce telomerase activity, which is therefore called the catalytic component of telomerase.

Artificially induced expression of the gene for the catalytic component of telomerase (by introducing the gene using genetic engineering methods) makes the cell culture immortal, that is, capable of dividing indefinitely, thereby canceling the Hayflick limit for culture. Telomerase is expressed in stem, sex, and some other types of cells in the body, which must constantly divide for the functioning of certain tissues (for example, intestinal epithelial cells). Ordinary somatic cells of the body are devoid of telomerase activity. Cells of 85% of cancerous tumors have telomerase activity; therefore, telomerase activation is considered to be one of the activator factors of the cell leading to a malignant transformation of a cancer cell.

Geroprotective Test of Formula 1 Compounds:

The initial number of fruit fly adults during the first six hours after emergence was subjected to ether anesthesia and placed in individual glass cups (from 5 to 10 virgin females and males in each). The cultures were assigned individual numbers. Subsequently, the dead individuals were regularly counted visually in each glass separately, without ether anesthesia, after which the surviving flies were transferred to a fresh medium, while maintaining the serial number of the glass. The size of each fruit flies cohort ranged in number from between about 100 to about 500 individuals.

The age and percent living fruit flies data were used with the below Survival Curve Equation: $Y=100/(1+EXP_{10}((MT_{50}-X)\times HS))$ wherein X is the age of the Fruit Flies cohort, and wherein Y is the percentage of living individuals in the Fruit Flies cohort. For each drug compound tested on these fruit flies, the experimental data was fit by a regression of the Survival Curve Equation to obtain a best $MT_{50}$ value and a best HS value. The $MT_{50}$ parameter is a close analogue to the average life expectancy. Thus, hereinafter the inventors treat the MT50 value to be the same as the Median Life Span (MLS) of the fruit flies in each experiment. Because the $MT_{50}$ was calculated using the least squares regression method, the $MT_{50}$ is also the standard regression coefficient, and such coefficients can be compared using a Fisher's "F-test" statistics test. The coefficients of determination for the regression model in all cases was greater than 90%.

The HS parameter is a calculated slope for experimental data fit to the survival curve equation. Thus HS parameter is analogous to the slope calculated by the Hill Equation. The HS as it is used by the inventors is an indirect estimator of the maximum life span (MLS). The Survivor Curve Equation value for Y asymptotically approached zero with the increasing age of the fruit flies cohort. The inventors elected to define the Expected Maximum Life Duration (EMLD) to be the X axis value when the value of Y (Y being the proportion of living fruit fly individuals) was 0.1%.

Below Table 8 tabulates the MLS (median life span for the tested synthetic Benzimidazole Formula I compounds which were introduced into the Fruit Flies feed as a 1% solution spray.

Table 8 compounds data is also presented in FIGS. 8, 9 and 10.

TABLE 8

Median life span for the tested synthetic Benzimidazole Formula 1 compounds which were introduced into the Fruit Flies feed as a 1% solution spray

| | Females | | Males | |
|---|---|---|---|---|
| Substance | MLS (day) | EMLD (day) | MLS (day) | EMLD (day) |
| Control | 26 ± 2 | 30.0 | 21 ± 1 | 23.0 |
| IIIa | 35 ± 5 | | 33 ± 5 | |
| IIIb | 44 ± 5 | | 42 ± 6 | |
| IIIc | 32 ± 6 | | 30 ± 5 | |
| IId | 37 ± 5 | | 39 ± 6 | |
| IIIe | 38 ± 5 | | 36 ± 5 | |
| IIIf | 32 ± 5 | | 30 ± 5 | |
| IIIg | 30 ± 5 | | 30 ± 5 | |
| IIIh | 52 ± 5 | | 57 ± 5 | |
| IIIi | 42 ± 6 | | 42 ± 6 | |
| Va | 40 ± 5 | | 44 ± 6 | |
| Vb | 33 ± 5 | | 37 ± 5 | |
| Vc | 37 ± 5 | | 35 ± 5 | |
| Vd | 43 ± 6 | | 42 ± 6 | |
| Ve | 40 ± 5 | | 38 ± 5 | |
| Vf | 43 ± 5 | | 42 ± 6 | |
| Vg | 44 ± 6 | | 40 ± 6 | |
| Vh | 43 ± 5 | | 44 ± 6 | |
| Vi | 32 ± 5 | | 31 ± 5 | |
| VIIa | 37 ± 5 | | 34 ± 5 | |
| VIIb | 38 ± 5 | | 33 ± 5 | |
| VIIc | 35 ± 5 | | 38 ± 5 | |
| VIId | 33 ± 5 | | 37 ± 5 | |
| VIIe | 30 ± 5 | | 33 ± 5 | |
| VIIf | 36 ± 5 | | 37 ± 5 | |
| VIIg | 33 ± 5 | | 39 ± 5 | |
| VIIh | 39 ± 5 | | 43 ± 6 | |
| VIIi | 42 ± 6 | | 48 ± 7 | |
| IXa | 54 ± 8 | | 59 ± 8 | |
| IXb | 55 ± 6 | | 57 ± 8 | |
| IXc | 34 ± 5 | | 42 ± 5 | |
| IXd | 37 ± 5 | | 36 ± 5 | |
| IXe | 35 ± 5 | | 38 ± 5 | |
| IXf | 22 ± 5 | | 26 ± 5 | |
| IXg | 43 ± 6 | | 44 ± 6 | |
| XIa | 50 ± 7 | | 57 ± 7 | |
| XIb | 43 ± 6 | | 44 ± 6 | |

TABLE 8-continued

Median life span for the tested synthetic Benzimidazole Formula 1 compounds which were introduced into the Fruit Flies feed as a 1% solution spray

| | Females | | Males | |
|---|---|---|---|---|
| Substance | MLS (day) | EMLD (day) | MLS (day) | EMLD (day) |
| XIc | 40 ± 6 | | 42 ± 6 | |
| XId | 33 ± 5 | | 35 ± 5 | |
| XIe | 36 ± 5 | | 38 ± 5 | |
| XIf | 37 ± 5 | | 36 ± 5 | |
| XIg | 35 ± 5 | | 39 ± 5 | |
| XIh | 40 ± 6 | | 44 ± 6 | |
| XIi | 47 ± 6 | | 48 ± 7 | |
| XIIIa | 40 ± 6 | | 38 ± 5 | |
| XIIIb | 35 ± 5 | | 35 ± 5 | |
| XIIIc | 55 ± 7 | | 59 ± 7 | |
| XIIId | 44 ± 6 | | 45 ± 6 | |
| XIIIe | 40 ± 5 | | 39 ± 5 | |
| XIIIf | 45 ± 6 | | 45 ± 6 | |
| XIIIg | 32 ± 5 | | 33 ± 5 | |
| XIIIh | 54 ± 8 | | 59 ± 8 | |
| XIIIi | 43 ± 6 | | 45 ± 6 | |
| XVa | 49 ± 7 | | 55 ± 9 | |
| XVb | 47 ± 6 | | 48 ± 7 | |
| XVc | 45 ± 6 | | 43 ± 6 | |
| XVd | 49 ± 8 | | 48 ± 7 | |
| XVe | 44 ± 6 | | 46 ± 5 | |
| XVf | 40 ± 5 | | 42 ± 6 | |
| XVg | 67 ± 9 | | 66 ± 9 | |
| XVh | 55 ± 8 | | 54 ± 8 | |
| XVi | 50 ± 8 | | 55 ± 7 | |

The experimental data shows that nearly all of the tested benzimidazole derivatives prolonged the life of the fruit flies. Some of the tested benzimidazole derivative compounds were surprisingly more effective in providing a geroprotection (an anti-geriatric action) for the *Drosophila* fruit flies, based on the criteria of extending the MLS of the flies by up to between 3 to 4 fold. Preferred compounds of the invention are synthetic Benzimidazole Formula I compounds Nos. IIIh, IXa, IXb, XIa, XIIIh, XVa, XVg, XVh, and XVi. These preferred compounds extended the median life span (MLS) of the fruit flies up to 50 days or more whereas the MLS of the control (normal) fruit flies was 21-26 days. A more preferred compound is the synthetic Benzimidazole Formula I compound No. XVg which extended the lifespan of *Drosophila* by nearly 3 fold to 70 days. The chemical structure for Compound No. XVg is drawn and named below.

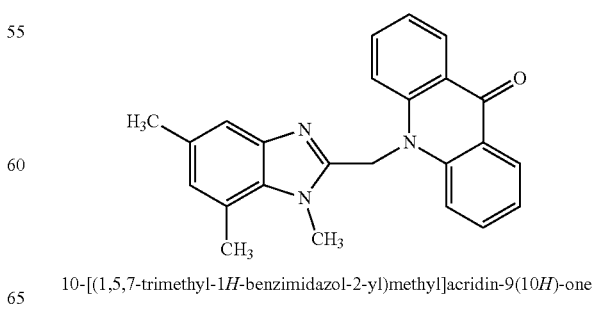

10-[(1,5,7-trimethyl-1*H*-benzimidazol-2-yl)methyl]acridin-9(10*H*)-one

What is claimed is:
1. A benzimidazole of formula I
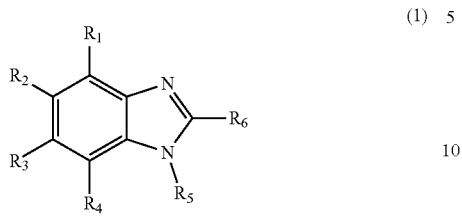 (1)
wherein substituents $R_1$, $R_2$, $R_3$, and $R_4$ are selected from the group consisting H, $CH_3$, $C_2H_5$, Br, Cl, I, F, CN, and $NO_2$,
wherein substituent $R_5$ is selected from the group consisting of H, $CH_3$, and $C_2H_5$, and wherein substituent $R_6$ is
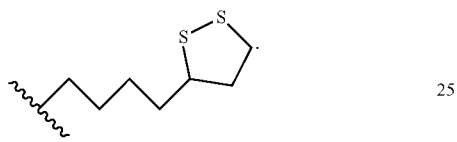
* * * * *